(12) United States Patent
Homyk et al.

(10) Patent No.: US 9,642,923 B2
(45) Date of Patent: May 9, 2017

(54) ENGINEERED PARTICLES WITH POLARIZATION CONTRAST AND ALIGNMENT CONTROL FOR ENHANCED IMAGING

(71) Applicant: Verily Life Sciences LLC, Mountain View, CA (US)

(72) Inventors: Andrew Homyk, Redwood City, CA (US); Victor Marcel Acosta, San Francisco, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 327 days.

(21) Appl. No.: 14/188,634

(22) Filed: Feb. 24, 2014

(65) Prior Publication Data
US 2015/0238636 A1 Aug. 27, 2015

(51) Int. Cl.
*A61B 5/1455* (2006.01)
*A61K 49/00* (2006.01)
(Continued)

(52) U.S. Cl.
CPC ........ *A61K 49/0017* (2013.01); *A61B 5/1455* (2013.01); *A61B 5/1468* (2013.01);
(Continued)

(58) Field of Classification Search
None
See application file for complete search history.

(56) References Cited

U.S. PATENT DOCUMENTS 6,123,920 A 9/2000 Gunther et al.
6,979,574 B1 12/2005 Kotitz et al.
(Continued)

FOREIGN PATENT DOCUMENTS

WO 2005/094902 10/2005

OTHER PUBLICATIONS

International Searching Authority, International Search Report and Written Opinion for PCT/US2015/015609 mailed May 22, 2015, 11 pages.

*Primary Examiner* — Eric Winakur
*Assistant Examiner* — Marjan Fardanesh
(74) *Attorney, Agent, or Firm* — McDonnell, Boehnen, Hulbert & Berghoff LLP

(57) ABSTRACT

An engineered particle for detecting analytes in an environment includes an electromagnetic receiver that is configured to preferentially receive electromagnetic radiation of a specified polarization relative to the orientation of the electromagnetic receiver. The engineered particle additionally includes an energy emitter coupled to the electromagnetic receiver such that a portion of electromagnetic energy received by the electromagnetic receiver is transferred to and emitted by the energy emitter. The engineered particles are functionalized to selectively interact with an analyte. The engineered particle can additionally be configured to align with a directed energy field in the environment. The selective reception of electromagnetic radiation of a specified polarization and/or alignment with a directed energy field can enable orientation tracking of individual engineered particles, imaging in high-noise environments, or other applications. A method for detecting properties of the analyte of interest by interacting with the engineered particle is also provided.

12 Claims, 17 Drawing Sheets

(51) Int. Cl.
  *A61B 5/00* (2006.01)
  *G01N 21/00* (2006.01)
  *A61B 5/1468* (2006.01)
  *A61B 8/08* (2006.01)
  *A61B 5/05* (2006.01)
  *A61B 5/055* (2006.01)
  *A61B 5/145* (2006.01)
  *B82Y 15/00* (2011.01)
  *B82Y 30/00* (2011.01)
  *G01R 33/56* (2006.01)
  *A61B 8/00* (2006.01)

(52) U.S. Cl.
  CPC ...... *A61B 5/14546* (2013.01); *A61B 5/14558* (2013.01); *A61B 5/681* (2013.01); *A61B 5/7435* (2013.01); *A61K 49/0093* (2013.01); *A61B 5/0022* (2013.01); *A61B 5/0051* (2013.01); *A61B 5/0093* (2013.01); *A61B 5/0095* (2013.01); *A61B 5/055* (2013.01); *A61B 5/0515* (2013.01); *A61B 5/14532* (2013.01); *A61B 8/4227* (2013.01); *A61B 8/481* (2013.01); *B82Y 15/00* (2013.01); *B82Y 30/00* (2013.01); *G01N 21/00* (2013.01); *G01R 33/5601* (2013.01)

(56) References Cited

U.S. PATENT DOCUMENTS

| | | |
|---|---|---|
| 7,639,359 B2 | 12/2009 | Chung et al. |
| 2005/0255044 A1 | 11/2005 | Lomnes et al. |
| 2009/0196828 A1 | 8/2009 | Suijver |
| 2010/0105026 A1 | 4/2010 | Bruckl et al. |
| 2010/0133488 A1 | 6/2010 | Giakos |
| 2013/0195979 A1 | 8/2013 | Tersigni |
| 2014/0017810 A1 | 1/2014 | Kimura |

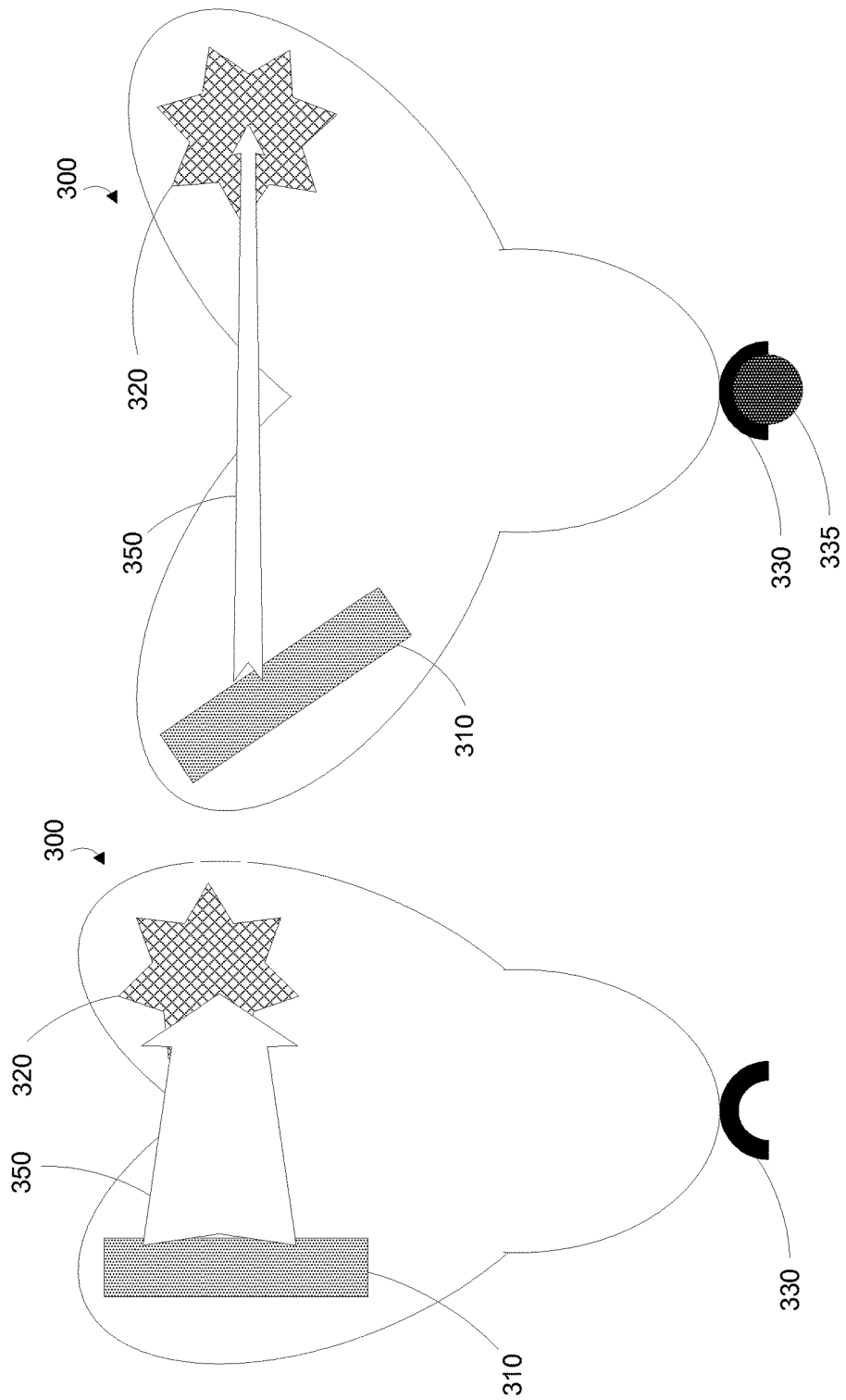

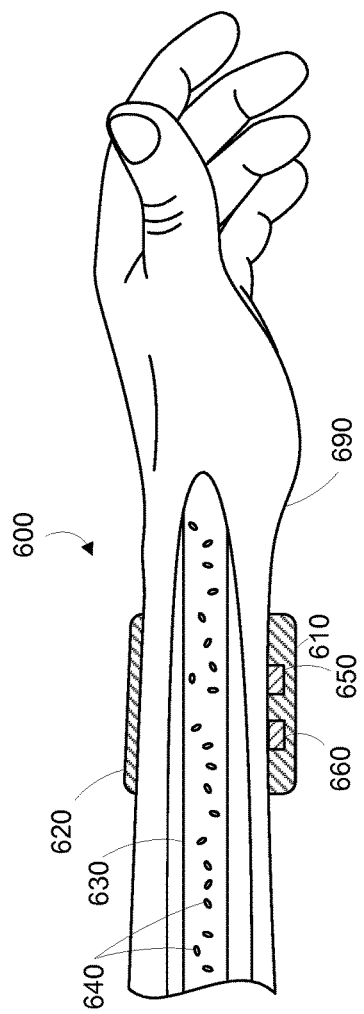
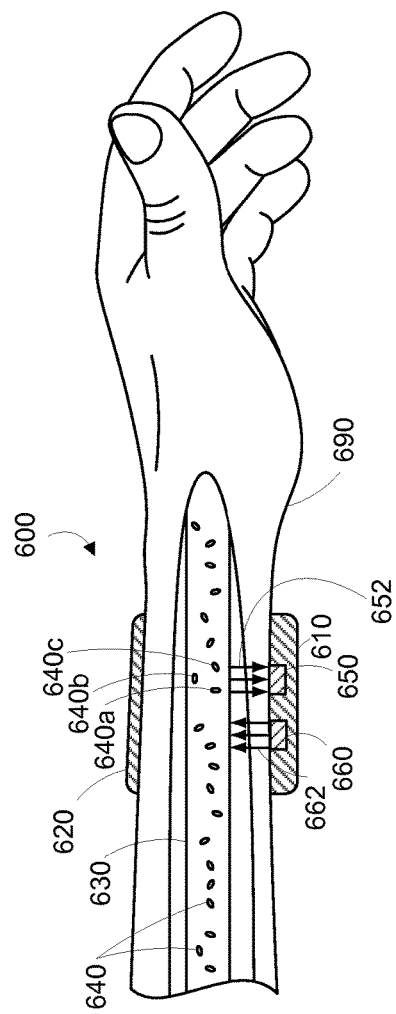

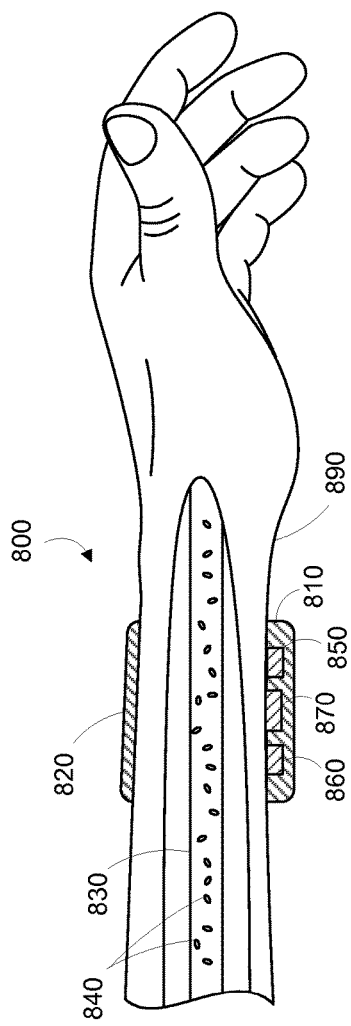
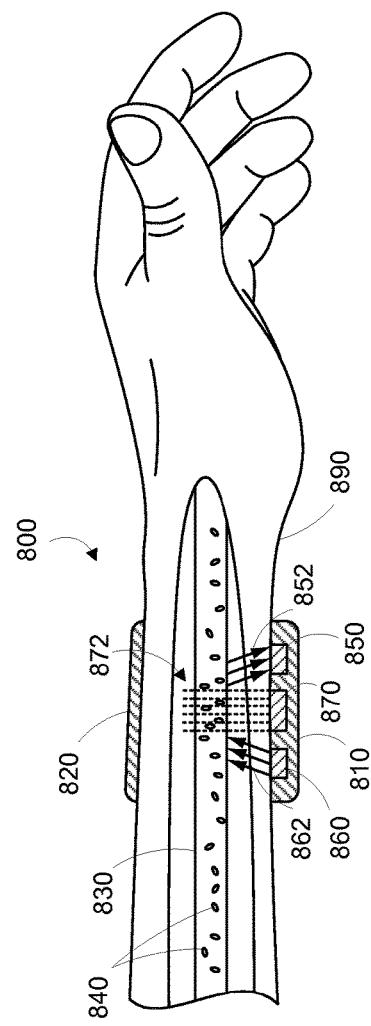

ENGINEERED PARTICLES WITH POLARIZATION CONTRAST AND ALIGNMENT CONTROL FOR ENHANCED IMAGING

BACKGROUND

Unless otherwise indicated herein, the materials described in this section are not prior art to the claims in this application and are not admitted to be prior art by inclusion in this section.

A number of scientific methods have been developed in the medical field to evaluate physiological conditions of a person by detecting and/or measuring one or more analytes in a person's blood or other environment. The one or more analytes could be any analytes that, when present in or absent from the body, or present at a particular concentration or range of concentrations, may be indicative of a medical condition or health state of the person. The one or more analytes could include enzymes, reagents, hormones, proteins, cells or other molecules.

SUMMARY

Some embodiments of the present disclosure provide a method including: (i) exposing an environment to electromagnetic radiation, wherein the environment includes engineered particles, wherein each engineered particle includes at least one electromagnetic receiver that receives electromagnetic energy in response to the exposure of the environment to the electromagnetic radiation, wherein the at least one electromagnetic receiver is configured to receive polarized electromagnetic radiation that is aligned with an axis of the at least one electromagnetic receiver more than polarized electromagnetic radiation that is not aligned with the axis of the at least one electromagnetic receiver, wherein each engineered particle includes at least one energy emitter, wherein the engineered particles are functionalized to selectively interact with an analyte in the environment, and wherein the at least one electromagnetic receiver has a level of coupling with the at least one energy emitter such that a portion of the electromagnetic energy received by the at least one electromagnetic receiver is transferred to the at least one energy emitter and a portion of the transferred energy is emitted by the at least one energy emitter; and (ii) detecting one or more properties of the energy emitted by the engineered particles in response to the exposure to the electromagnetic radiation.

Some embodiments of the present disclosure provide an engineered particle including (i) at least one electromagnetic receiver, wherein the at least one electromagnetic receiver is configured to receive polarized electromagnetic radiation that is aligned with an axis of the at least one electromagnetic receiver more than polarized electromagnetic radiation that is not aligned with the axis of the at least one electromagnetic receiver; and (ii) at least one energy emitter, wherein the at least one energy emitter has a level of coupling with the at least one electromagnetic receiver such that a portion of electromagnetic energy received by the at least one electromagnetic receiver is transferred to the at least one energy emitter, and wherein the at least one energy emitter is configured to emit a portion of the transferred energy, wherein the engineered particle is functionalized to selectively interact with an analyte.

Some embodiments of the present disclosure provide an engineered particle including: (i) at least one conductive nanorod, wherein the at least one conductive nanorod is configured to receive polarized electromagnetic radiation that is aligned with an axis of the at least one conductive nanorod more than polarized electromagnetic radiation that is not aligned with the axis of the at least one conductive nanorod; (ii) at least one particle of superparamagnetic iron oxide, wherein the at least one particle of superparamagnetic iron oxide is configured to align the engineered particle with a magnetic field; and (iii) at least one energy emitter, wherein the at least one energy emitter is coupled to the at least one conductive nanorod such that a portion of electromagnetic energy received by the at least one conductive nanorod is transferred to the at least one energy emitter, and wherein the at least one energy emitter is configured to emit a portion of the transferred energy, wherein the engineered particle is functionalized to selectively interact with an analyte.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3A is a schematic diagram of an example engineered particle.

FIG. 3B is a schematic diagram of the example engineered particle of FIG. 3A, bound to an analyte.

FIG. 6A is side partial cross-sectional view of a wrist-mounted device, while on a human wrist.

FIG. 6B is side partial cross-sectional view of the wrist-mounted device of FIG. 6A, while on a human wrist.

FIG. 8A is side partial cross-sectional view of a wrist-mounted device, while on a human wrist.

FIG. 8B is side partial cross-sectional view of the wrist-mounted device of FIG. 8A, while on a human wrist.

DETAILED DESCRIPTION

Figure 1:
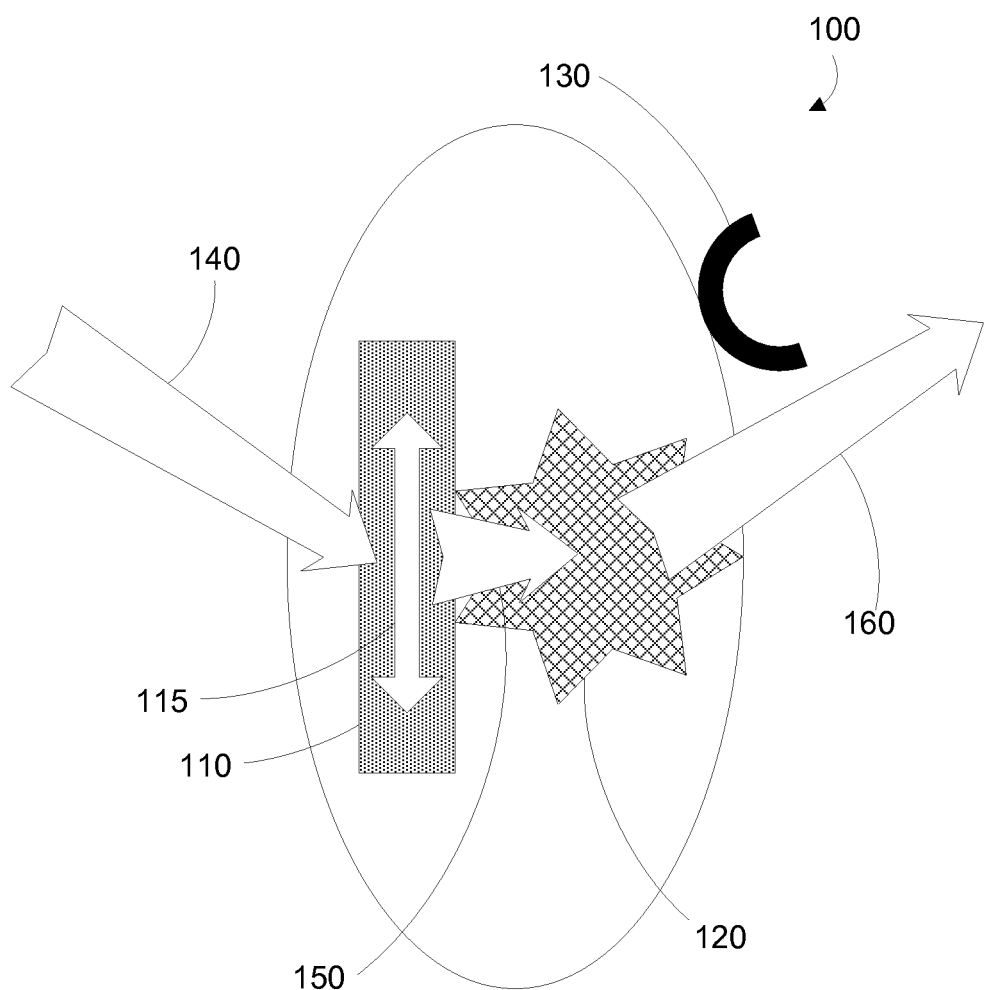
FIG. 1 is a schematic diagram of an example engineered particle.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of an analyte is desired. The environment may be any living or non-living body or a portion thereof, a fluid conduit, a fluid reservoir, etc. For example, one of skill in the art will recognize that the embodiments disclosed herein may be used to sense analytes present in a water system. Moreover, while the present disclosure describes embodiments for use in vivo, one of skill in the art will also recognize that in vitro applications are possible as well. Accordingly, the environment may also include a test tube or other vessel for holding a fluid.

I. Overview

Biological environments can be interrogated electromagnetically (e.g., imaged using visible, infrared, ultraviolet, radio frequency (RF) or other types of electromagnetic radiation) for diagnostic or other purposes. Electromagnetic (e.g., optical) interrogation of certain biological environments can be difficult, however, in cases where the electromagnetic radiation passes through highly absorbing or scattering media, such as tissue. Imaging through such media can, in some cases, be achieved using adaptive optical systems, optical coherence tomography, photoacoustic tomography, ultrasound, or other techniques. In such approaches, sensitivity and/or specificity can be improved through the use of polarization-specific information. Disclosed herein are contrast agents, and methods and systems for using contrast agents, which can provide such polarization-specific information. In an example, a contrast agent (e.g., an engineered particle) could have a non-uniform response to electromagnetic radiation of different polarizations (e.g., receiving more or, absorbing more of, scattering more of, and/or interacting more with electromagnetic energy having a particular orientation relative to the contrast agent more than electromagnetic energy having a different orientation). This non-uniform polarization response could be used to detect the contrast agent in a biological or other environment that has a relatively uniformly response to illumination by polarized electromagnetic radiation (e.g., polarized light). For example, the environment containing the contrast agent could be illuminated by light having different polarizations, and the degree of reception of, absorption of, scattering or, or other interaction with light energy by the contrast agent could be detected to determine the presence, concentration, location, orientation, or other properties of the contrast agent.

In some examples, a contrast agent can include one or more engineered particles, where the engineered particles include one or more chemicals, nanostructures, or other components configured to operate individually or in concert. For example, an engineered particle could include an optical absorber configured to absorb polarized light that is aligned with an axis of the optical absorber more than polarized light that is not aligned with the axis of the optical absorber. The engineered particle could also include an energy emitter coupled to the optical absorber, such that at least a portion of optical energy of a particular polarization that is absorbed by the optical absorber is transferred to and emitted by the energy emitter. In this way, an energy emitter can be made to have a non-uniform response to light of different polarizations by being incorporated into an engineered particle that includes a polarization-selective optical absorber. Such engineered particles could additionally be configured to selectively interact with an analyte and used to detect the presence, concentration, or other properties of the analyte.

In some examples, an engineered particle including a polarization-selective optical absorber and an energy emitter coupled to the optical absorber could have properties that change in response to interaction of the engineered particle with an analyte. In some examples, the level of coupling between the optical absorber and the energy emitter could be affected by interaction between the engineered particle and the analyte. For example, the engineered particle could include a protein that is configured to selectively interact with the analyte. Interaction (e.g., binding) between the protein and the analyte could cause a change in the configuration of the protein such that the distance between a first and a second region of the protein changed. The optical absorber could be attached to the first region of the protein and the energy emitter could be attached to the second region of the protein such that the distance between the optical absorber and the energy emitter was related to interaction between the protein and the analyte. Coupling of energy between the optical absorber and the energy emitter could be related to the distance between the optical absorber and the energy emitter such that the interaction between the engineered particle and the analyte could be detected by illuminating the engineered particle and detecting energy emitted by the engineered particle in response to the illumination. Other configurations of engineered particle, wherein one or more properties of the absorption of light by the particle and/or emission of energy by the particle are related to interaction of the engineered particle with an analyte, are anticipated.

In some examples, an engineered particle could include a polarization-selective optical absorber and a light energy emitter coupled to the optical absorber. For example, the light energy emitter could be a Raman dye and/or a fluorophore. The light energy emitter could emit light of a specified frequency, polarization, or other property. In some examples, an engineered particle could include a polarization-selective optical absorber and an energy emitter configured to emit acoustical energy. For example, the energy emitter could be heated by optical energy absorbed by the optical absorber and the heating of the energy emitter could cause a quick expansion of the engineered particle, resulting in the production of an acoustic wave. Additionally or alternatively, the energy emitter could be configured to emit the optical energy (e.g., as infrared radiation), and the emitted energy could be detected using an infrared sensor, bolometer, or by some other means.

In some examples, an engineered particle including a polarization-selective optical absorber and an energy emitter coupled to the optical absorber could be configured to align with a directed energy field. The directed energy field could be, for example, a magnetic field, an electric field, an optical field, or an acoustic field. The engineered particle could be configured to have an axis, and could be configured such that the directed energy field causes the engineered particle to rotate to align the axis with the field. For example, the engineered particle could include a particle of superparamagnetic iron oxide that is configured to align the engineered particle with a magnetic field.

In some examples, one or more properties of an engineered particle including a polarization-selective optical absorber and an energy emitter coupled to the optical absorber and configured to align with an energy field could be detected by creating and/or controlling a directed energy field around the engineered particle, illuminating the engineered particle, and detecting one or more properties of energy emitted by the particle in response to the illumination. In some examples, the directed energy field could be controlled to align the engineered particles such that the optical absorbers were oriented relative to illumination having a specified polarization that is preferentially absorbed by the aligned optical absorbers. Additionally or alternatively, the directed energy field could be changed over time, such that the level of absorption of the polarized illumination by engineered particles over time is related to the changes in the field over time. For example, a directed energy field could be generated to align the engineered particles. Generation of the directed energy field could then be discontinued, and one or more properties of the engineered particles and/or of analytes interacting with the engineered particles could be determined based on changes in the level of absorption of the polarized illumination by engineered particles over time after the generation of the directed energy field is discontinued. Other methods of creating and/or changing a directed energy field to effect a change in an engineered particle are anticipated.

The engineered particle could be functionalized with receptors, proteins, antibodies, DNA sequences, and/or other materials such that the engineered particle selectively interacts with the one or more analytes. The engineered particle can be functionalized by covalently or otherwise attaching or associating a bioreceptor that specifically binds or otherwise interacts with a particular analyte. The bioreceptor can be an antibody, peptide, nucleic acid, phage, bacteria, virus, aptamer, or any other molecule with a defined affinity for a target analyte. Other compounds or molecules, such as fluorophores or autofluorescent or luminescent markers or non-optical contrast agents (e.g. acoustic impedance contrast, RF contrast and the like), which may assist in interrogating the engineered particles in an environment, may also be attached to or included as part of the engineered particles.

The engineered particles could be introduced into a biological or other environment. Light could be emitted into the environment such that the optical absorbers of the engineered particles absorb some light energy and couple a portion of the absorbed light energy to the energy emitters or the engineered particles such that the energy emitters emit a portion of the coupled energy. One or more properties of the emitted energy could be detected and used to determine one or more properties of the engineered particles in the environment (e.g., the location of individual engineered particles, whether individual engineered particles are interacting with an analyte, the orientation of individual engineered particles). The determined one or more properties of the engineered particles in the environment could be used to determine the presence, location, concentration, and/or other properties of the one or more analytes in the environment. For example, the environment could be a human body and the one or more analytes could be cancer cells. The imaging agent could be functionalized to selectively bind to the cancer cells and/or to elements of the cancer cells. The presence of the cancer cells in the human body could be detected by detecting one or more properties of the engineered particles in the human body.

In some examples, the engineered particles could be illuminated by light having a particular polarization and the emitted intensity of the energy emitted by the energy emitters of the engineered particles in response to the illumination could be detected. Additionally or alternatively, some other property of the energy emitted by the engineered particles in response to illumination could be detected (e.g., polarization of the emitted energy). This method could be used to detect the engineered particle in high-noise and/or low-signal-to-noise-ratio environments. Additionally or alternatively, this method could be used to detect the orientation of individual engineered particles.

The engineered particle could include other elements in addition to the one or more optical absorbers and energy emitters as described herein. Those of skill in the art will understand a "particle" in its broadest sense and that it may take the form of any fabricated material, a molecule, tryptophan, a conductive or nonconductive nanorod, a quantum dot, a virus, a phage, a complex of nanodiamonds, etc. Further, a particle may be of any shape, for example, spheres, rods, non-symmetrical shapes, etc.

A system may include one or more data collection systems for interrogating, in a non-invasive manner, engineered particles present in an environment, such as a lumen of subsurface vasculature in a particular local area of a human. In some examples, the system includes an energy sensor configured to detect a response signal emitted from energy emitters in engineered particles in a portion of subsurface vasculature. In some examples, the system may also include an interrogating light source for transmitting illumination that can penetrate into a portion of subsurface vasculature, or another environment, and an energy sensor for detecting energy that is emitted by energy absorbers in engineered particles in the portion of subsurface vasculature, or other environment, in response to absorption of the illumination by optical absorbers in the engineered particles.

The above described system may be implemented as a wearable device. The term "wearable device," as used in this disclosure, refers to any device that is capable of being worn at, on or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The energy sensor, light source, and, in some examples, a processor, may be provided on the wearable device. In other embodiments, the above described system may be implemented as a stationary measurement device to which a user must be brought into contact or proximity with or as a device that may be temporarily placed or held against a body surface during one or more measurement periods.

Note that, herein, embodiments of optical absorbers configured to absorb polarized light that is aligned with an axis of the optical absorber more than polarized light that is not aligned with the axis of the optical absorber are intended to represent a broader class of electromagnetic receivers configured to receive polarized electromagnetic radiation that is aligned with an axis of the electromagnetic receiver more than polarized electromagnetic radiation that is not aligned with the axis of the electromagnetic receiver. That is, examples, embodiments, processes, methods, and descriptions included herein that specify the presence of, interaction with, or use of such optical absorbers should be understood to apply to the more general class of electromagnetic receivers. Electromagnetic receivers could be configured to receive, absorb, scatter, or otherwise couple with electromagnetic radiation having one or more wavelengths and/or spectral profiles, and could include ultraviolet, visible, infrared, microwave, radio, or other bands of electromagnetic energy.

Receiving electromagnetic radiation could involve a variety of processes. Receiving electromagnetic radiation could include absorption of one or more photons, scattering one or more photons, and/or reflecting one or more photons. Receiving electromagnetic radiation could additionally or alternatively include absorbing, scattering, reflecting, refracting, or otherwise interacting with an electromagnetic wave or other time-varying electromagnetic field. Receiving electromagnetic radiation could include any interaction or coupling with an electromagnetic wave or photon such that a portion of the energy of the electromagnetic wave or photon, depending on the direction and/or degree of polarization of the electromagnetic wave or photon relative to an axis of an electromagnetic receiver receiving the electromagnetic radiation, was transferred to the electromagnetic receiver and/or to the immediate environment of the receiver. For example, the electromagnetic receiver could absorb, via two-photon absorption, energy from two photons, and this energy could be coupled (e.g., through an alternating electric field surrounding the receiver and induced by a plasmon resonance of the receiver) to an energy emitter. In another example, the electromagnetic receiver could be configured to scatter energy from an electromagnetic wave such that an energy emitter proximate to the receiver was able to emit more energy than if the energy emitter was exposed to the same electromagnetic wave and not proximate to the receiver. Other configurations of electromagnetic receivers and energy emitters and examples of receiving electromagnetic radiation are anticipated.

Further, instances where interaction with optical absorbers or devices configured to interact with optical absorbers are described are to be understood to additionally describe, with necessary modifications familiar to one of skill in the art, interactions with or devices configured to interact with the more general class of electromagnetic receivers. For example, where a description includes emission of optical energy into an environment containing optical absorbers, it is to be understood that the description could additionally or alternatively apply (with necessary modifications familiar to one or skill in the art) to emission of electromagnetic energy into an environment containing electromagnetic receivers. For example, a description including a light source or light emitter should be understood to additionally or alternatively describe an ultraviolet light source or emitter, an infrared light source or emitter, a radio frequency (RF) energy source or emitter, or some other electromagnetic energy source or emitter.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Engineered Particles

In some examples, information about analytes in an environment can be obtained by detecting properties of an imaging agent, for example, engineered particles as described herein. FIG. 1 illustrates an example engineered particle 100 that includes an optical absorber 110, an energy emitter 120, and a bioreceptor 130. The optical absorber 110 is configured to absorb incident polarized light that has a direction of polarization parallel to a preferred direction 115 of the optical absorber 110. The optical absorber 110 and the energy emitter 120 are coupled such that some of an optical energy 140 that is transmitted by polarized light that is incident on the optical absorber 110 and that has a direction of polarization parallel to the preferred direction 115 is coupled as a transferred energy 150 to the energy emitter 120 and emitted into the environment of the engineered particle as an emitted energy 160.

The bioreceptor 130 can be designed to selectively bind or otherwise recognize a particular analyte. For example, the bioreceptor 130 can include a variety of structures, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), plasmids. In some examples, the engineered particle 100 could include a bioreceptor onto which is attached at least one optical absorber and at least one energy emitter. The bioreceptor 130 (or a combination of bioreceptors) could be chosen to cause the engineered particle 100 to selectively interact with an analyte that includes a target of the bioreceptor 130. For example, the bioreceptor 130 could be a bioreceptor that selectively interacts with a protein or other element that is expressed by cancer cells to enable the use of the engineered particle 100 to detect cancer cells. The engineered particle 100 can be introduced into a person's blood stream by injection, ingestion, inhalation, transdermally, or in some other manner.

Elements of the engineered particle 100, including the optical absorber 110, energy emitter 120, and bioreceptor 130, can be incorporated into a single particle in a variety of configurations. In some examples, the elements of the engineered particle 100 can be attached to another element, for example, a superstructure or a backbone. For example, the engineered particle could include a protein, nanorod, nanotube, or some other structural element to which the optical absorber 110, energy emitter 120, and bioreceptor 130 are attached. Alternatively, one of the elements of the engineered particle 100 could act as a superstructure or backbone. For example, the optical absorber 110 could include a conductive nanorod, and the bioreceptor 130 and energy emitter 120 could be attached to the surface of the optical absorber 110. Additionally or alternatively, multiple elements of the engineered particle 100 could be implemented as a single component. For example, the energy emitter 120 and the bioreceptor 130 could be part of a single recombinant protein that has a fluorescent moiety and an analyte-specific binding site. The recombinant protein could be attached to the optical absorber 110 such that optical energy absorbed by the optical emitter 110 could be coupled to the fluorescent moiety of the recombinant protein. A configuration of elements of the engineered particle 100 could be chosen to affect one or more properties of the engineered particle 100, e.g., to tailor the level of coupling between the optical absorber 110 and the energy emitter 120. Other configurations of elements of the engineered particle 100 are anticipated.

Elements of the engineered particle 100 can be attached to one another and/or assembled together by a variety of methods. Surfaces of individual elements can be attached to each other by covalent bonds, adsorption, electrostatic attraction, Van der Waals forces, or by some other mechanism. Individual elements could be treated or altered to facilitate attachment to other elements. For example, the surface of individual elements could be altered such that the surface is terminated in carboxyl groups. Additionally or alternatively, a coating or other substance could be applied to, bound to the surface of, or otherwise attached to individual element(s) of the engineered particle 100 such that individual elements(s) can be attached to the coating or other substance, such that the individual elements are attached together. More than one bioreceptor 130 could be included in the engineered particle 100. Elements of the engineered particle 100 could be assembled using self-assembly or some other method to ensure a specified spatial, functional, electronic, or other relationship between elements of the engineered particle 100. In some examples, complexes of the same or different bioreceptors could be attached directly or indirectly to elements of the engineered particle 100 such that the engineered particle more selectively interacted with a target analyte.

The analyte could be a clinically-relevant analyte. A clinically-relevant analyte could be any analyte that, when present or absent, or present at a particular concentration or range of concentrations, may be indicative of a medical condition or indicative that a medical condition may be imminent. For example, the clinically-relevant analyte could be an enzyme, hormone, protein, cell, or other biological element. In one relevant example, certain protein biomarkers expressed by a cell are known to be predictive of the cell being a cancer cell. By providing engineered particles functionalized with a bioreceptor that will selectively bind to these target protein biomarkers, interaction with the engineered particles (e.g., illuminating the particles, detecting properties of energy emitted by the particles, and/or generating a directed field to orient the engineered particles) could be used to determine one or more properties of the cell (e.g., the location of the cell, whether the cell was being transported by blood in a lumen of subsurface vasculature of a person's body, that the cell was a cancer cell).

The optical absorber 110 configured to preferentially absorb incident polarized light that has a direction of polarization parallel to a preferred direction 115 of the optical absorber 110 (that is, the optical absorber 110 that has an anisotropic absorption spectrum and/or that is optically anisotropic) can be composed of a variety of materials and configured in a variety of ways. In some examples, the optical absorber 110 is composed of a conductive or semi-conductive material and configured to have a geometry that causes the optical absorber 110 to absorb more energy from polarized light having a specified direction of polarization that is aligned with one or more axes of the geometry of the optical absorber 110 relative to polarized light having other directions of polarization. Additionally or alternatively, the optical absorber 110 could be configured to selectively absorb light having some other polarization property relative to the optical absorber 110, including circularly polarized light of a specific handedness, elliptically polarized light of a specific handedness, major axis direction, or degree of ellipticity. For example, the optical absorber could be a nanorod composed of a conductive material (e.g., gold, carbon nanotube, etc.). In other examples, the optical absorber 110 could include quantum dots, quantum plates, or other structures composed of semiconductors or other materials whose optical properties are determined by quantum-scale effects. The optical absorber 110 could be configured to absorb optical energy through two-photon or multi-photon excitation. The optical absorber 110 could include fluorophores having polarization-specific absorption characteristics. The optical absorber could include other optically anisotropic elements, including birefringent elements, crystals, crystal defects, defects and/or dopants in a nanodiamond, polarizers, liquid crystals, dichroic elements, and layered structures that include multiple layers of conductors, semiconductors, and insulators. Other examples of optical absorber 110 are possible as well.

The energy emitter 120 is configured to receive transferred energy 150 from the optical absorber 110 and to emit a portion of the transferred energy 150 as emitted energy 160. The emitted energy 160 can be light energy, an electrical field, a magnetic field, an acoustic wave, an electromagnetic wave, or any other energy capable of being detected and used to determine one or more properties of the engineered particle 100 and/or an analyte bound to the engineered particle. In some examples, the transferred energy 150 is light energy, and the energy emitter 120 is one or more of a fluorophore, chromophore, dye, pigment, Raman dye, crystal defect and/or dopant, quantum dot, nanoscale light-emitting doped semiconductor, or some other light-emitting structure. In some examples, the transferred energy 150 is an electric field, and the energy emitter 120 is a nano- or micro-scale antenna. In some examples, the emitted energy 160 is an acoustic wave, and the energy emitter 120 includes elements that transduce the transferred energy 150 into a mechanical displacement of the environmental medium surrounding the engineered particle. For example, the energy emitter 120 could experience thermal expansion due to the transferred energy 150 such that an acoustical wave was transmitted into the environmental medium surrounding the energy absorber 120. In some embodiments, this could include the energy emitter 120 comprising a bimetallic and/or piezoelectric unimorph or bimorph. Additionally or alternatively, the energy emitter 120 could include piezoelectric materials according to some other configuration, and the transferred energy 150 could take the form of an electric field and/or electric current. Other examples of energy emitter 120 are possible as well.

The coupling between the optical absorber 110 and the energy emitter 120 could take many forms. The coupling could include the optical absorber 110 generating an electric field, a magnetic field, an electromagnetic field and/or wave, an acoustic wave or vibration, a surface plasmon, or some other energy-carrying phenomenon in response to illumination of the optical absorber 110 such that the energy emitter 120 receives a portion of the transferred energy 150. For example, the optical absorber 110 could be a conductive nanorod configured to transduce at least a portion of incoming optical energy 140 into a surface plasmon resonance, such that a time-varying electric field is generated around the optical absorber 110. The energy emitter 120 could be configured such that it is able to transduce this time-varying electrical field into an emitted energy 160 (e.g., the energy emitter 120 could be a fluorophore), and the engineered particle 100 could be configured such that the energy emitter 120 is situated within the electric field generated by the optical absorber 110 in response to illumination. In some examples, the transferred energy 150 is a thermal energy; that is, the optical absorber 110 transduces incoming optical energy 140 into heat energy, and the heat energy is transferred to the energy emitter 120. Other configurations of the engineered particle 100, optical absorber 110, and energy emitter 120 to provide a level of coupling between the optical absorber 110 and the energy emitter 120 are possible as well.

Figure 2B:
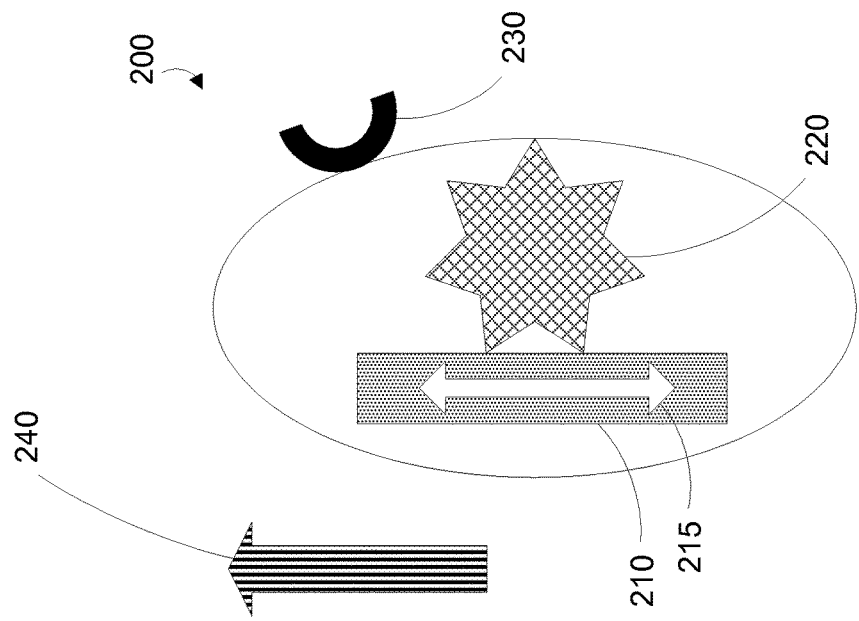
FIG. 2B is a schematic diagram of the example engineered particle of FIG. 2A aligned with a directed energy field.
Figure 2A:
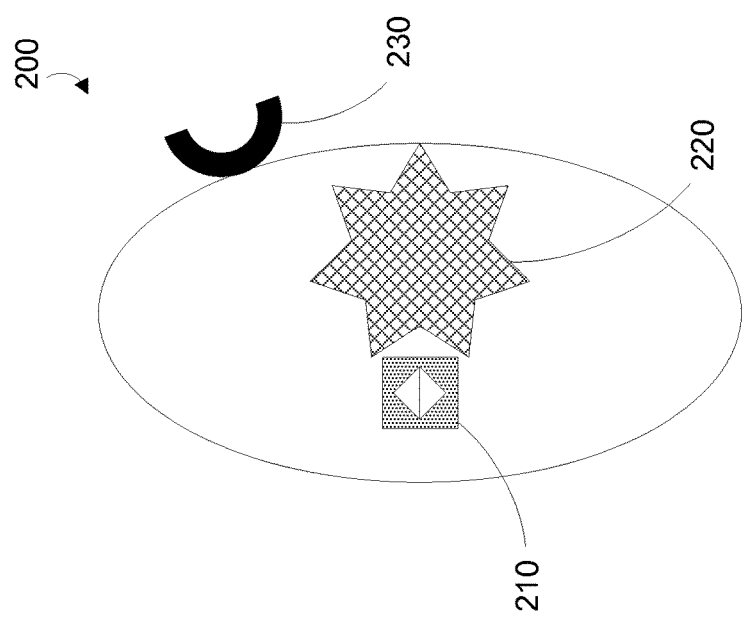
FIG. 2A is a schematic diagram of an example engineered particle experiencing a torque due to a directed energy field.

A property of an engineered particle, including the optical anisotropy of an optical absorber in an engineered particle, could be related to the environment of the engineered particle. For example, the optical anisotropy of the optical absorber could be induced or modulated by an exterior energy or directed energy field. FIG. 2A illustrates an engineered particle 200 that includes an optical absorber 210, an energy emitter 220, and a bioreceptor 230. FIG. 2B illustrates the same engineered particle 200, optical absorber 210, energy emitter 220, and bioreceptor 230 being exposed to a directed energy field 240. Exposure to the directed energy field 240 causes the optical absorber 210 to absorb incident polarized light that has a direction of polarization parallel to a preferred direction 215 of the optical absorber 210 more than incident polarized light having other directions of polarization. The preferred direction 215 can be controlled or influenced by the directed energy field 240. In some examples, the preferred direction 215 is induced or created in response to the directed energy field 240 being applied. In other examples, the preferred direction 215 exists prior to application of the directed energy field 240 but becomes oriented in a particular way when the directed energy field 240 is applied.

The external energy field 240 could be a magnetic field, an electric field, an electromagnetic field, an acoustic field, or some other directed energy field. The effects of the external energy field 240 on the engineered particle 200 could be contingent on the continued application or generation of the external energy field 240 or could be permanent or semi-permanent; that is, the application of the external energy field 240 could cause a change in state of the engineered particle 200 that persists after the external energy field 240 is deactivated, reduced, or otherwise changed. The effects of the external energy field 240 on the engineered particle 200 could be related to the direction, magnitude, polarization, gradient, divergence, curl, frequency or rate of change of the field, or other properties of the external energy field 240 in the environment of the engineered particle. Alternatively, the effects of the external energy field 240 on the engineered particle 200 could be substantially unrelated to one or more of the aforementioned properties of the external energy field 240. For example, the external energy field 240 could be a directed radio frequency (RF) electromagnetic field that is capable of causing the optical absorber 210 to thermally expand, causing the optical absorber 210 to expand anisotropically, such that the optical absorber 210 absorbs incident polarized light that has a direction of polarization parallel to the preferred direction 215 of the optical absorber 210 than incident polarized light having other directions of polarization.

The optical absorber 210 or other elements of the engineered particle 200 can have properties related to an external energy field 240 by being configured in a variety of ways. The elements of the engineered particle 200 could include one or more of magnetostrictive, ferromagnetic, ferromagnetic, paramagnetic, superparamagnetic, electrostrictive, piezoelectric, dielectric, or other materials. The engineered particle 200 could include thermal and/or piezoelectric unimorphs or bimorphs. Elements of the engineered particle 200 could have multiple stable states or conformations, and the state of those elements could be changed by the application and/or removal of an external energy field to the engineered particle 200. Other configurations and components of an engineered particle are anticipated.

A property of an engineered particle could be related to the environment of the engineered particle. For example, a level of energy coupling between an optical absorber and an energy emitter in the engineered particle could be modulated by chemicals, analytes or other elements in the environment of the engineered particle. FIG. 3A illustrates an engineered particle 300 that includes an optical absorber 310, an energy emitter 320, and a bioreceptor 330. The degree to which optical energy absorbed by the optical absorber 310 is transferred to the energy emitter 320 is represented by the level of coupling 350 between the optical absorber 310 and the energy emitter 320. FIG. 3B illustrates the same engineered particle 300, optical absorber 310, energy emitter 320, and bioreceptor 330 when the engineered particle 300 is bound to an analyte 335. Binding with the analyte 335 causes the engineered particle 300 to change configuration, such that the optical absorber 310 and the energy emitter 320 are separated by a greater distance in 3B than in 3A. As a result, the level of coupling 350 in the configuration of particle 300 shown in FIG. 3B is reduced compared to the configuration of particle 300 shown in FIG. 3A.

In the example shown in FIGS. 3A and 3B, the binding of the analyte 335 causes the level of coupling 350 to decrease by increasing a distance between the optical absorber 310 and energy emitter 320. Alternatively, the engineered particle 300 could be configured in other ways such that interaction with the analyte 335 causes an increase or decrease in the level of coupling 350. In some examples, the coupling of energy between the optical absorber 310 and the energy emitter 320 could rely on a specific relation between the optical absorber 310 and the energy emitter 320, for example, a specified relative orientation of one or both of the optical absorber 310 and the energy emitter 320. For example, the optical absorber 310 could transduce incoming illumination into a surface plasmon resonance, such that a time-varying electric field is generated around the optical absorber 310. Further, the time-varying electric field could have a distribution relative to the orientation of the optical absorber 310; for example, the time-varying electric field could have a larger amplitude along both directions of an axis of the optical absorber 310. The energy emitter 320 could be configured such that it is able to transduce such a time-varying electrical field into an emitted energy (e.g., the energy emitter 320 is a fluorophore) and the engineered particle 300 could be configured such that the energy emitter 320 is situated within the electric field generated by the optical absorber 310 in response to illumination (i.e., along the axis of the optical absorber 310). The level of coupling 350 between the optical absorber 310 and the energy emitter 320 could be modulated by rotating the optical absorber 310 such that the energy emitter 320 was no longer situated along the axis of the optical absorber 320. Other configurations of the engineered particle 300 such that the level of coupling 350 between the optical absorber 310 and the energy emitter 320 are related to binding of the engineered particle 300 with an analyte 335, or related to some other factor or property of the environment of the engineered particle 300, are anticipated.

Other factors in or properties of the environment of the engineered particle 300 could affect the level of coupling 350 between the optical absorber 310 and the energy emitter 320 or could affect some other property of the engineered particle 300. For example, the optical anisotropy of the optical absorber 310, the direction of a preferred direction of the optical absorber 310, the wavelength, spectrum, linewidth of an emission peak, or some other property of light illumination emitted by the energy emitter 320, the selectivity of the bioreceptor 330 for the analyte 335, or some other property of the engineered particle could be related to a factor in or property of the environment of the engineered particle 300. Further, the temperature, pH, osmolarity, dielectric constant of a solvent in the environment, concentration of an ion or metal, or some other property of the environment could affect one or more properties of the engineered particle 300.

Figure 4B:
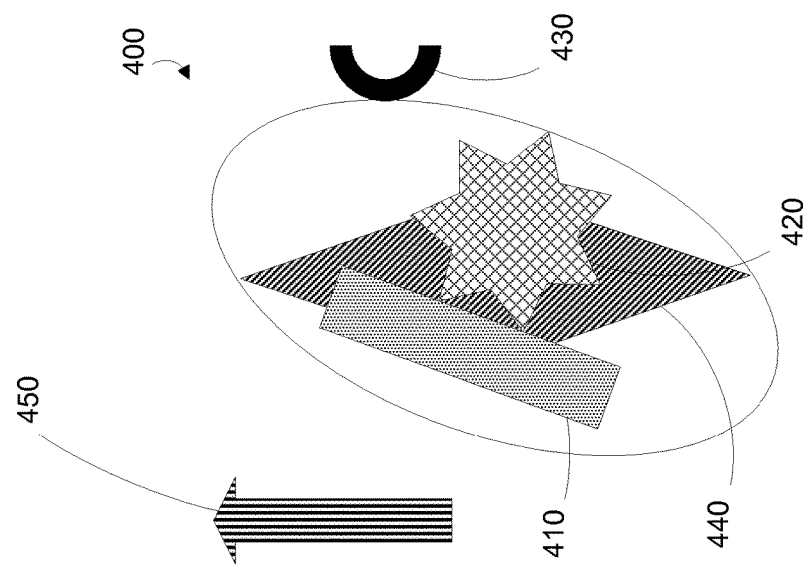
FIG. 4B is a schematic diagram of the example engineered particle of FIG. 4A, where an optical receiver of the engineered particle is being affected by an energy field.
Figure 4A:
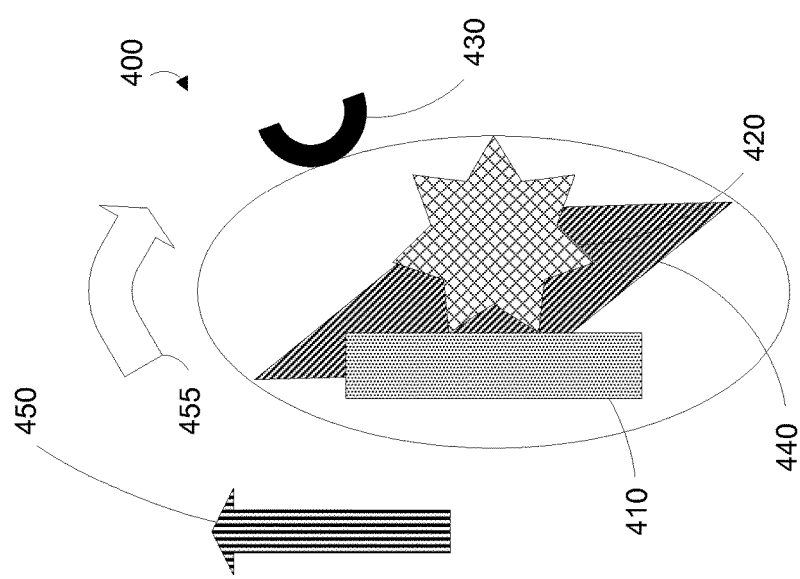
FIG. 4A is a schematic diagram of an example engineered particle.

The orientation of an engineered particle could be related to the environment of the engineered particle. For example, the orientation of the engineered particle could be controlled by a directed energy field. FIG. 4A illustrates an engineered particle 400 that includes an optical absorber 410, an energy emitter 420, a bioreceptor 430, and a magnetic dipole 440. The engineered particle 400 is being exposed to a directed magnetic field 450 such that the engineered particle 400, through the magnetic dipole 440, experiences an orienting torque 455. FIG. 4B illustrates the same engineered particle 400, optical absorber 410, an energy emitter 420, a bioreceptor 430, and a magnetic dipole 440 being exposed to the magnetic field 450 and oriented such that the magnetic dipole 440 is aligned with the direction of the magnetic field 450.

The engineered particle 400 in FIGS. 4A and 4B is meant as an illustrative example of a class of engineered particles that are configured to align with a directed energy field. The magnetic dipole 440 could be replaced with some other element to enable the engineered particle to be aligned with a directed magnetic field. Correspondingly, the magnetic field 450 could be replaced with some other energy field such that the orientation of the engineered particle experiences a force to align with a direction of the energy field. Further, the magnetic dipole 440 or other orientable element could be part of one or more other components of the engineered particle. For example, the optical absorber 410 could be a nanorod of superparamagnetic iron oxide coated in gold, such that the iron oxide enabled the orientability of the engineered particle 400 and the gold coating enabled the nanorod to selectively absorb polarized light of one orientation (e.g., along the long axis of the nanorod) more than polarized light of other orientations.

The magnetic field 450 could instead be some other directed energy field, for example, an electric field, an electromagnetic field, an acoustic field, or some other directed energy field. The effects of the directed energy field on the orientation of the engineered particle 400 could be related to the direction, magnitude, polarization, gradient, divergence, curl, frequency or rate of change of the field, or other properties of the directed energy field in the environment of the engineered particle 400. Correspondingly, the magnetic dipole 440 could instead include conductive nanostructures (loops, antennas, plates), quantum dots, dielectrics, induced dipoles, electric dipoles, molecular dipoles, acoustic elements having characteristic anisotropic vibrational modes, or other materials or elements to enable the orientation of the engineered particle to be affected by a directed energy field. The element of the engineered particle 400 enabling the orientation of the engineered particle 400 by a directed energy field could be induced by some external factor and/or impermanent. For example, an RF field could induce a dipole in an element or chemical of the engineered particle 400, and a directed energy field (possibly the same RF field that induced the dipole in the engineered particle 400) could align the orientation of the engineered particle 400 by transmitted a torque through the induced dipole or by otherwise influencing the induced dipole of the engineered particle 400.

Functionalized engineered particles that include optical absorbers and optical emitters as described herein may additionally include other elements. Engineered particles can include more than one optical absorber, more than one energy emitter, and/or more than one bioreceptor. Engineered particles could include biodegradable or non-biodegradable materials. For example, the particles may include polystyrene. Engineered particles that include non-biodegradable materials may be provided with a removal means to prevent harmful buildup in the body or other environment. Generally, the particles may be designed to have a long half-life so that they remain in the vasculature, body fluids, or other environment to enable their use in detecting analytes over an extended period of time. Depending on the lifetime of the engineered particles, however, new batches of engineered particles may be periodically introduced into the environment.

Engineered particles can be used in diagnostic procedures, or even in therapy to destroy, damage, or otherwise modify a specific target in a body, such as antitumor therapy or targeted chemotherapy. Such therapy could occur continuously or in response to some condition; for example, detection that an instance of the target was in range of some modification means could trigger the activation of the modification means to destroy, damage, or otherwise modify the target. The engineered particles may be designed to remove from the body or destroy the target analyte once bound to a bioreceptor of the engineered particle. The target analyte could be heated, lysed, denatured, porated, or otherwise altered or damaged to reduce or eliminate a deleterious function or effect of the target analyte. Additional functional groups may be added to the particles to signal that the particles can be removed from the body through the kidneys, for example, once bound to the target analyte. The target analyte could be otherwise altered, folded, denatured, porated, or functionalized to cause some other process to occur to the target analyte, for example, to change the target analyte such that an element of a user's immune system acted to destroy, metabolize, or otherwise alter the target analyte.

Further, the engineered particles may be designed to either releasably or irreversibly bind to the target analyte. For example, if it is desired for the particles to participate in destruction or removal of the target analyte from the body, as described above, the particles may be designed to irreversibly bind to the target analyte. In other examples, the particles may be designed to release the target analyte after measurement has been made, either automatically or in response to an external or internal stimulus.

Those of skill in the art will understand the term "particle" in its broadest sense and that it may take the form of any fabricated material, a molecule, cryptophan, a virus, a phage, etc. Further, a particle may be of any shape, for example, spheres, rods, non-symmetrical shapes, etc., and may be made of a solid, liquid or gaseous material or combinations thereof. The particles can have a diameter that is less than about 20 micrometers. In some embodiments, the particles have a diameter on the order of about 10 nanometers to 1 micrometer. In further embodiments, small particles on the order of 10-100 nanometers in diameter may be assembled to form a larger "clusters" or "assemblies on the order of 1-10 micrometers. In this arrangement, the assemblies would provide the signal strength of a larger particle, but would be deformable, thereby preventing blockages in smaller vessels and capillaries.

The term "binding" is understood in its broadest sense to include any detectable interaction between an engineered particle and a target analyte. For example, some engineered particles may be functionalized with compounds or molecules, such as fluorophores or autofluorescent, luminescent or chemiluminescent markers, which generate a responsive signal when the particles bind to the target analyte without the input of a stimulus. In other examples, the functionalized engineered particles may produce a different responsive signal in their bound versus unbound state in response to an external stimulus, such as an electromagnetic, acoustic, optical, or mechanical energy. In some examples, binding of the particles could be detected by a change in the movement of the engineered particles. For example, the orientation and/or location of the particles could be detectable, and the rotation and/or translation of the particles could be affected by binding of the particles. For example, unbound engineered particles could exhibit changes in orientation at a certain rate, while bound particles could exhibit changes in orientation at a detectably lower rate, due to the inertia or other properties of the bound analyte.

Further, the engineered particles may include a paramagnetic or ferromagnetic material or be functionalized with a magnetic moiety. The magnetic properties of the particles can be exploited in magnetic resonance detection schemes to enhance detection sensitivity. In another example, an external magnet may be used to locally collect, orient, or otherwise selectively manipulate the particles in an area of an environment. Such collection may enhance the signal for detection and/or increase a signal-to-noise-ratio of detection by correlating modulation of the orientation, location, or other properties of the engineered particles with a detected property of the engineered particles (for example, the amplitude of an emitted light).

III. Illustrative Methods for Detecting Engineered Particles in an Environment

Figure 5:
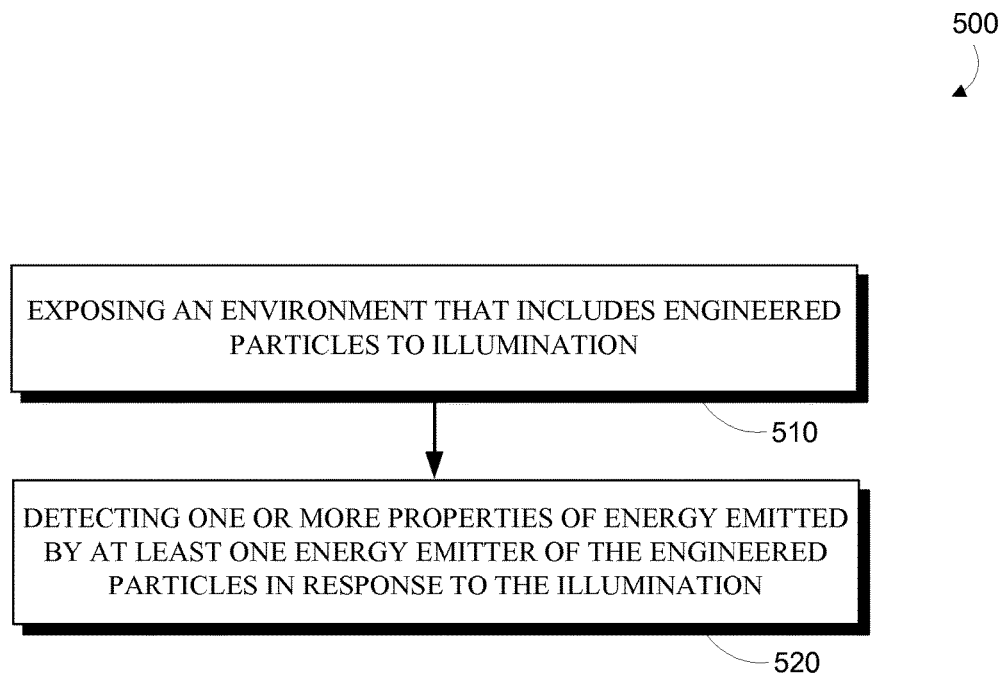
FIG. 5 is a flowchart of an example method.

FIG. 5 is a flowchart of a method 500 for operating a device to detect the presence, location, orientation, concentration, or other properties of engineered particles in an environment. Each engineered particle in the environment includes at least one optical absorber coupled to at least one energy emitter and is functionalized to selectively interact with an analyte in the environment. The at least one optical absorber is configured to absorb polarized light that is aligned with an axis of the at least one optical absorber more than polarized light that is not aligned with the axis of the at least one optical absorber. Further, there is a level of coupling between the at least one optical absorber and the at least one energy emitter, such that a portion of illumination energy absorbed by the at least one optical absorber is transferred to the at least one energy emitter and emitted by the energy emitter into the environment.

The method 500 includes exposing the environment to illumination 510 such that the at least one optical absorbers of engineered particles in the environment absorb a portion of the illumination energy and the at least one energy emitters emit a portion of the absorbed energy into the environment. This can include emitting illumination having a specific wavelength or spectral profile, such that the illumination can be absorbed by the optical absorbers, emitted by the energy emitters, efficiently transmitted through the environment, or other considerations. Exposing the environment to illumination 510 can include emitting illumination having a specified linear, circular, or other polarization. Further, exposing the environment to illumination 510 can include emitting illumination having different properties at different points in time. For example, it could include emitting illumination having a first amplitude, wavelength, spectral profile, polarization, or other property at a first point in time and emitting illumination having a second amplitude, wavelength, spectral profile, polarization, or other property at a second point in time. Exposing the environment to illumination 510 could additionally include emitting illumination such that some other element of the environment emitted light in response. For example, illumination could be emitted such that a fluorophore in the environment emitted light in response.

The method 500 additionally includes detecting one or more properties of the energy emitted by the at least one energy emitter in the engineered particles in response to the illumination 520. This can include detecting the amplitude, wavelength, spectrum, linewidth of an emission peak, degree of polarization, orientation of polarization, location, or other properties of the emitted light. It can also include detecting one or more properties of light emitted by the at least one energy emitter of the engineered particles at more than one point in time. For example, the location of light emitted by the at least one energy emitter in response to illumination could be detected at a plurality of points in time. The respective plurality of detected locations of emitted light could then be used to infer respective locations of engineered particles in the environment at the plurality of points in time.

The method 500 could include additional steps or elements in addition to exposing the environment to illumination 510 and detecting one or more properties of the energy emitted by the at least one energy emitter in response to the illumination 520. For example, the method 500 could include introducing the engineered particles into the environment (e.g., injecting, ingesting, transdermally transferring, or otherwise introducing the engineered particles into a lumen of vasculature of a human, applying the engineered particles to an in vitro or other non-human biological environment, applying the engineered particles to a non-biological environment or other methods). The method 500 could include determining one or more properties of the engineered particles based on the detected one or more properties of the light emitted by the at least one energy emitter. For example, the method 500 could include determining the location of an engineered particle based on the location of light emitted by the at least one energy emitter. The method 500 could further include determining one or more properties of the analyte based on determined one or more properties of particle(s). For example, the determined location, orientation, or other properties of one or more engineered particles could be used to determine the location of one or more instances of the analyte. Other additional and/or alternative elements of method 500 are anticipated.

In some examples, the environment described in relation to the method 500 above could be a portion of vasculature in a human body. For example, the biological environment could be a lumen of subsurface vasculature of a wearer of a device that is configured to implement and execute elements of the method 500. In some examples, the analyte in the environment could be a cell. For example, the environment could be a tissue of a human, and the analyte could be a cancer cell. The engineered particles could be functionalized to selectively interact with the cancer cell by being attached to a bioreceptor that is selectively receptive to one or more elements of the cancer cell, e.g., a membrane-spanning protein. Other examples of environments, analytes, configurations of engineered particle functionalization, and other elements are anticipated.

FIGS. 6A-6B, and 8A-8B are partial cross-sectional side views of a human wrist illustrating the operation of various examples of a wrist-mounted device. In the example shown in FIGS. 6A and 6B, the wrist-mounted device 600 includes a measurement platform 610 mounted on a strap or wristband 620 and oriented on the anterior side 690 of the wearer's wrist. Measurement platform 610 is positioned over a portion of the wrist where subsurface vasculature 630 is easily observable. Functionalized, engineered particles 640 that include optical absorbers coupled to energy emitters have been introduced into a lumen of the subsurface vasculature 630 by one of the means discussed above. The optical absorber of an individual engineered particle is configured to absorb polarized light that is aligned with an axis of the optical absorber more than polarized light that is not aligned with the axis of the optical absorber. In this example, measurement platform 610 includes a data collection system having both an energy sensor 650 and a light source 660. FIG. 6A illustrates the state of the subsurface vasculature 630 when wrist-mounted device 600 is not interrogating engineered particles 640 in the subsurface vasculature 630. The state of the subsurface vasculature 630 during detection is illustrated in FIG. 6B. At this time, light source 660 is transmitting illumination 662 into the portion of subsurface vasculature and light sensor 650 is detecting one or more properties of an emitted energy 652 emitted by energy emitters in engineered particles 640 in response to the illumination 662. The emitted energy 652 can have one or more properties related to one or more properties of the engineered particles 640. One or more properties of the engineered particles 640 can be related to one or more properties of an analyte in the subsurface vasculature 630.

The wrist-mounted device 600 could be configured to determine one or more properties of the engineered particles 640 based on the detected one or more properties of the emitted energy 652. Additionally or alternatively, the wrist-mounted device 600 could be configured to convey information about the detected one or more properties of the emitted energy 652 to another system, and the other system could be configured to determine one or more properties of the engineered particles 640 based on the conveyed information. For example, the location of engineered particles 640 in the subsurface vasculature 630 could be determined based on the location of the emitted energy 652 (e.g., the energy sensor 650 could include a grid of energy-sensing pixels or transducers, and the location of an individual engineered particle 640 could be determined by calculating a centroid of active pixels or transducers of the energy sensor 650 during a period when the light source 660 is transmitting the illumination 662).

The wrist-mounted device 600 could be configured to determine one or more properties of the analyte in the subsurface vasculature 630 based on determined one or more properties of the engineered particles 640. Additionally or alternatively, the wrist-mounted device 600 could be configured to convey information about the determined one or more properties of the engineered particles 640 to another system, and the other system could be configured to determine one or more properties of the analyte based on the conveyed information. For example, the location of an individual instance of the analyte (e.g., a single cancer cell) in the subsurface vasculature 630 could be determined based on the determined location(s) of one or more engineered particles 640 over time. A correlation in the locations of more than one engineered particles 640 over time could be used to determine that the more than one engineered particles 640 are bound to the individual instance of the analyte and that the location of the individual instance of the analyte is proximate to the determined locations of the more than one engineered particles 640.

Due to the optical anisotropy of the optical absorbers in the engineered particles, the amplitude or other properties of energy emitted by energy emitters in an individual engineered particle can be related to the polarization and/or orientation of polarization of light illuminating the individual engineered particle. The orientations of the example individual engineered particles 640a, 640b, 640c in FIG. 6B are illustrated by the orientation of the ellipses used to illustrate the individual engineered particles in the subsurface vasculature 630. In particular, first individual engineered particle 640a has a vertical orientation relative to the wrist-mounted device 600, second individual engineered particle 640b has a horizontal orientation relative to the wrist-mounted device 600, and third individual engineered particle 640c has an angled orientation relative to the wrist-mounted device 600.

The use of engineered particles containing optically anisotropic optical absorbers can allow for increased-contrast imaging relative to contrast agents that do not have optically anisotropic elements. For example, it could be assumed that background tissues of the wearer (e.g., the walls of the subsurface vasculature) have a substantially isotropic absorption spectrum relative to polarized light generated by light source 660 having different directions of polarization. The light source 660 could transmit illumination 662 having different polarizations or other properties at respective points in time, and one or more properties of energy emitted by the engineered particles 640 could be detected by the energy sensor 650 at the respective points in time. The detected one or more properties of the emitted energy could change between different points in the respective points in time, and one or more properties of the individual engineered particles could be determined based on the detected one or more properties of the emitted energy at the respective points in time.

For example, the light source 660 could produce vertically polarized light at a first point in time and could produce horizontally polarized light at a second point in time. The first individual engineered particle 640a could emit energy detectable by the energy sensor 650 at the first point in time and could emit substantially no energy at the second point in time, allowing the amplitude of energy emitted by the first individual engineered particle 640a to be used to determine the orientation of the first individual engineered particle 640a. A similar method could be used to determine the orientation of other engineered particle 640, e.g., 640b, 640c.

The binding or other interaction between one or more individual engineered particles to an analyte could be determined based on a specified polarization of illumination emitted by the light source 660 and/or one or more properties of energy emitted by energy emitters in the individual engineered particles. In some examples, the aforementioned information could be used to determine the orientation and/or relative orientation of individual engineered particles. The orientation of an individual engineered particle over time could be used to infer that the engineered particle is bound due to a detectable difference between the behavior (in terms of the change of orientation and/or relative orientation over time) of an unbound engineered particle and an engineered particle to the analyte. For example, an individual engineered particle and an individual engineered particle bound to the analyte could be assumed to change orientation according to a statistical model having one or more parameters that are different for the unbound engineered particle and the bound engineered particle/analyte complex (for example, a hydrodynamic volume, a relaxation time, an electrostatic radius, or some other parameter or variable). Other methods of determining whether an individual engineered particle is bound to an analyte, using wrist-mountable device similar to the wrist-mountable device 600 or using some other apparatus, are anticipated.

The binding and/or interaction of one or more individual engineered particles with an analyte could be determined based on a detectable change in one or more properties of the individual engineered particles. In some examples, binding of an engineered particle to an analyte could affect the level of coupling between an optical absorber and an energy emitter in the engineered particle. For example, binding of the analyte to the engineered particle could change a distance between or relative orientation of the optical absorber and the energy emitter, such that the portion of light energy absorbed by the optical absorber that is emitted by the energy emitter is changed. In some examples, the level of coupling between the optical absorber and the energy could be substantially zero in the bound or unbound state, such that detecting any energy being emitted by an energy emitter in an individual engineered particle could be used to determine that the individual engineered particle was unbound or bound, respectively, to the analyte. Other properties of the engineered particle could be affected by binding with an analyte, and these other property changes could be used to detect the binding of individual engineered particles to analytes.

Figure 7:
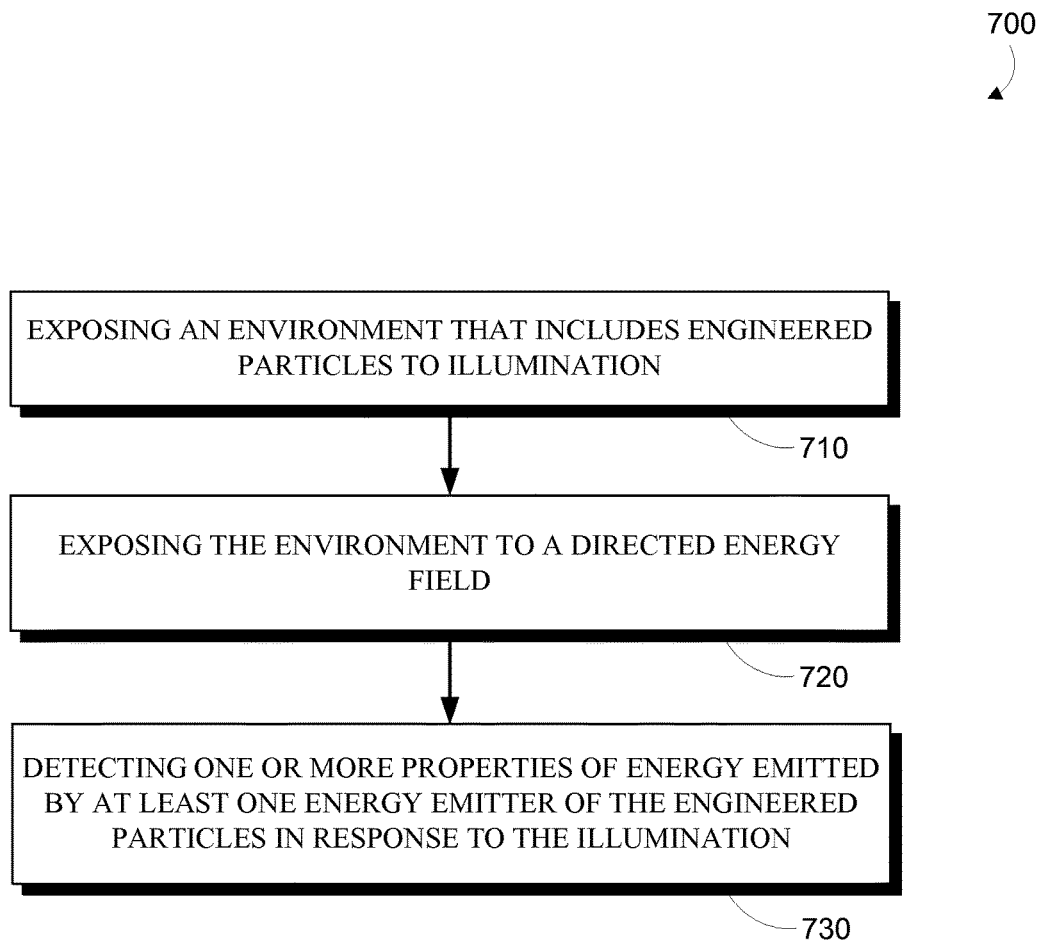
FIG. 7 is a flowchart of an example method.

FIG. 7 is a flowchart of a method 700 for operating a device to detect the presence, location, orientation, concentration, or other properties of engineered particles in an environment. Each engineered particle in the environment includes at least one optical absorber coupled to at least one energy emitter and is functionalized to selectively interact with an analyte in the environment. The at least one optical absorber is configured to absorb polarized light that is aligned with an axis of the at least one optical absorber more than polarized light that is not aligned with the axis of the at least one optical absorber. Further, there is a level of coupling between the at least one optical absorber and the at least one energy emitter, such that a portion of illumination energy absorbed by the at least one optical absorber is transferred to the at least one energy emitter and emitted by the energy emitter into the environment. The engineered particles are additionally configured to align with a directed energy field.

The method 700 includes exposing the environment to illumination 710 such that the at least one optical absorbers of engineered particles in the environment absorb a portion of the illumination energy and the at least one energy emitters emit a portion of the absorbed energy into the environment. This can include emitting illumination having a specific wavelength or spectral profile, such that the illumination can be absorbed by the optical absorbers, emitted by the energy emitters, efficiently transmitted through the environment, or other considerations. Exposing the environment to illumination 710 can include emitting illumination having a specified linear, circular, or other polarization. Further, exposing the environment to illumination 710 can include emitting illumination having different properties at different points in time. For example, it could include emitting illumination having a first amplitude, wavelength, polarization, or other property at a first point in time and emitting illumination having a second amplitude, wavelength, polarization, or other property at a second point in time. Exposing the environment to illumination 710 could additionally include emitting illumination such that some other element of the environment emitted light in response. For example, illumination could be emitted such that a fluorophore in the environment emitted light in response.

The method additionally includes exposing the environment to a directed energy field 720, such that engineered particles in a region of the environment experience a change in one or more properties due to the directed energy field. In some examples, the engineered particles become completely or partially aligned with some aspect of the directed energy field. In some examples, another property of the engineered particles, for example an optical anisotropy of an optical absorber, a level of coupling between an optical absorber and an energy emitter, or some other property is affected by one or more properties of the directed energy field. The energy field could be any of a variety of energy fields, including but not limited to magnetic fields, electric fields, electromagnetic fields, optical fields, RF fields, microwave fields, acoustic fields, ultrasonic fields, or other directed energy fields. Exposing the environment to a directed energy field 720 can result in an increased concentration engineered particles proximate to whatever means is employed to generate the directed energy field; for example, the directed energy field could magnetically attract the engineered particles in the environment to an electromagnet.

Further, exposing the environment to a directed energy field 730 can include generating directed energy fields having different properties at different points in time. For example, it could include generating a directed energy field having a first amplitude, wavelength, spectral profile, polarization, divergence, curl, or other property at a first point in time and generating a directed energy field having a second amplitude, wavelength, spectral profile, polarization, divergence, curl, or other property at a second point in time. For example, a first directed energy field could be generated at a first time such that engineered particles in the environment aligned in a horizontal direction relative to the means for generating the directed energy field. A second directed energy field could be generated at a second time such that engineered particles in the environment aligned in a vertical direction relative to the means for generating the directed energy field. One or more properties of illumination directed into the environment and/or energy emitted by particles in the environment at the first and second points in time, along with information about the directed energy field at the first and second points in time, could be used to determine one or more properties of engineered particles in the environment and/or of analytes in the environment.

The method 700 additionally includes detecting one or more properties of the light emitted by the at least one energy emitter in the engineered particles in response to the illumination 730. This can include detecting the amplitude, wavelength, spectrum, linewidth of an emission peak, degree of polarization, orientation of polarization, location, or other properties of the emitted light. It can also include detecting one or more properties of light emitted by the at least one energy emitter of the engineered particles at more than one point in time. For example, the location of light emitted by the at least one energy emitter in response to illumination could be detected at a plurality of points in time. The respective plurality of detected locations of emitted light could then be used to infer respective locations of engineered particles in the environment at the plurality of points in time.

The method 700 could include additional steps or elements in addition to exposing the environment to illumination 710, exposing the environment to a directed energy field 720, and detecting one or more properties of the energy emitted by the at least one energy emitter in response to the illumination 730. For example, the method 700 could include introducing the engineered particles into the environment (e.g., injecting, ingesting, transdermally transferring, or otherwise introducing the engineered particles into a lumen of vasculature of a human, applying the engineered particles to an in vitro or other non-human biological environment, applying the engineered particles to a non-biological environment or other methods). The method 700 could include determining one or more properties of the engineered particles based on the detected one or more properties of the light emitted by the at least one energy emitters, one or more properties of the emitted light, and/or one or more properties of the directed energy field. For example, the method 700 could include determining the location of an engineered particle based on the location of light emitted by the at least one energy emitters. The method 700 could further include determining one or more properties of the analyte based on determined one or more properties of engineered particle(s). For example, the a rate of change of particle orientation of one or more engineered particles in response to a controlled changed in a directed energy field could be used to that the engineered particle was bound to one or more instances of the analyte, and thus to determine the location of one or more instances of the analyte. Other additional and/or alternative elements of method 700 are anticipated.

In some examples, the environment described in relation to the method 700 above could be a portion of vasculature in a human body. For example, the biological environment could be a lumen of subsurface vasculature of a wearer of a device that is configured to implement and execute elements of the method 700. In some examples, the analyte in the environment could be a cell. For example, the environment could be a tissue of a human, and the analyte could be a cancer cell. The engineered particles could be functionalized to selectively interact with the cancer cell by being attached to a bioreceptor that is selectively receptive to one or more elements of the cancer cell, e.g., a membrane-spanning protein. Other examples of environments, analytes, configurations of engineered particle functionalization, and other elements are anticipated.

Similar to the system depicted in FIGS. 6A and 6B, FIGS. 8A and 8B illustrate a wrist-mounted device 800 including a measurement platform 810 mounted on a strap or wristband 820 and oriented on the anterior side 890 of the wearer's wrist. Functionalized, engineered particles 840 that include optical absorbers coupled to energy emitters and that are configured to align with a directed energy field have been introduced into a lumen of the subsurface vasculature 830 by one of the means discussed above. In this example, measurement platform 810 includes a data collection system having an energy sensor 850, a light source 860 and a field generator 870. FIG. 8A illustrates the state of the subsurface vasculature when measurement device 800 is not interrogating engineered particles 840 in the subsurface vasculature 830. The state of the subsurface vasculature 830 when measurement device 800 is active during a measurement period is illustrated in FIG. 8B. At this time, field generator 870 generates a directed energy field 872 sufficient to align engineered particles 840 present in a lumen of the subsurface vasculature 830 and to collect engineered particles 840 in a region proximal to the field generator 870. Light source 860 transmits illumination 862 into the portion of subsurface vasculature and energy sensor 850 is detecting one or more properties of emitted energy 852 emitted by energy emitters in the engineered particles 840 in response to the illumination 862. The emitted energy 852 can have one or more properties related to one or more properties of the engineered particles 840, the illumination 862, and/or the directed energy field 872. One or more properties of the engineered particles 840 can be related to one or more properties of an analyte in the subsurface vasculature 830 and/or one or more properties of the directed energy field 872.

Due to the optical anisotropy of the optical absorbers in the engineered particles, the amplitude or other properties of energy emitted by energy emitters in an individual engineered particle can be related to the polarization and/or orientation of polarization of light illuminating the individual engineered particle. This optical anisotropy could be used in combination with the ability control the orientation or other properties of the engineered particles using the field generator 870 to detect one or more properties of the engineered particles 840 or an analyte in the subsurface vasculature 830, even in circumstances where such detection would be difficult without using the field generator 870 (e.g., the subsurface vasculature contains turbid media, 'noise' energy (magnetic, electric, electromagnetic, acoustic), or some other confounding factor).

The use of engineered particles configured to align with an energy field and containing optically anisotropic optical absorbers can allow for increased-contrast imaging relative to contrast agents that do not configured in that way. In some examples, field generator 870 could generate a directed energy field 872 having amplitude, direction, polarity, or other properties at respective points in time, the light source 860 could generate illumination 862 having a linear polarization at the respective points in time, and one or more properties of energy emitted by the engineered particles 840 could be detected by the energy sensor 850 at the respective points in time. The detected one or more properties of the emitted energy could change between different points in the respective points in time, and one or more properties of the individual engineered particles could be determined based on the detected one or more properties of the emitted energy 852 and the one or more properties of the directed energy field 872 at the respective points in time.

For example, the field generator 870 could be operated to generate a directed energy field 872 at a first point in time such that the preferred direction of optical absorbers in the engineered particles 840 were aligned parallel to the direction of the linear polarization of the illumination 862. At a second point in time, the field generator 870 could be operated to generate a directed energy field 872 such that the preferred direction of optical absorbers in the engineered particles 840 were aligned perpendicular to the direction of the linear polarization of the illumination 862. As a result, the energy emitted by energy emitters in the engineered particles 840 at the first point in time could have one value, and the energy emitted by energy emitters in the engineered particles 840 at the second point in time could be substantially zero. The presence, location, or other properties of the engineered particles 840 could be determined by analyzing information generated by the energy sensor 870 at the first and second points in time and assuming that changes in the information between the first and second points in time are related substantially to the engineered particles 840. One or more properties of the illumination 862 could also be different between the first and second points in time, and this difference could additionally be used to determine one or more properties of the engineered particles 840.

The field generator 870 could additionally or alternatively be used to alter a property of the engineered particles 840. In some examples, the field generator 870 could generate a directed energy field 872 such that engineered particles 840 in a specified region had an induced, modulated, or otherwise changed property, including a coupling between an optical absorber and an energy emitter, an optical anisotropy of an optical absorber, or some other property. For example, the directed energy field 872 could be a magnetic or an electric field and could induce a change in the geometry of magnetostrictive or electrostrictive materials, respectively, in the optical absorbers of the engineered particles such that a property of the optical anisotropy of the optical absorbers was related to a property of the directed energy field. In another example, the directed energy field 872 could be an RF field configured such that engineered particles in a selected region were heated by the directed energy field 872. The heating of the engineered particles 840 could cause an element of the engineered particles 840 to deform (for example, a bimetallic element) such that one or more properties of the engineered particles 840 are changed due to the deformation (e.g., an optical anisotropy of an optical absorber, a level of coupling between an optical absorber and an energy emitter). Other uses or configurations of the energy field generator 870, directed energy field 872, and engineered particles 840 are anticipated.

The wrist-mounted device 800 could be configured to determine one or more properties of the analyte in the subsurface vasculature 830 based on determined one or more properties of the engineered particles 840. Additionally or alternatively, the wrist-mounted device 800 could be configured to convey information about the determined one or more properties of the engineered particles 840 to another system, and the other system could be configured to determine one or more properties of the analyte based on the conveyed information. For example, the location of an individual engineered particle could be determined using one or more of the techniques described herein. The field generator 870 could generate a directed energy field 872 and the change in orientation of the individual engineered particle in response to a change in the directed energy field 872 could be determined. One or more properties of the change in orientation of the individual engineered particle could be used to determine that the individual engineered particle was bound to an instance of the analyte and/or one or more properties of the analyte. For example, an individual engineered particle and an individual engineered particle bound to the analyte could be assumed to change orientation in response to changes in the directed energy field 872 according to a model having one or more parameters that are different for the unbound engineered particle and the bound engineered particle/analyte complex (for example, a hydrodynamic volume, a relaxation time, an electrostatic radius, or some other parameter or variable). Other methods of determining whether an individual engineered particle is bound to an analyte, using wrist-mountable device similar to the wrist-mountable device 800 or using some other apparatus, are anticipated.

The example embodiments described herein generally include a single variety of engineered particle used to image and/or determine one or more properties of an analyte in an environment. However, more than one type of engineered particle could be used to determine one or more properties of more than one respective analyte in an environment. Additionally or alternatively, one or more of the respective analytes could be components of an analyte of interest, e.g., the analyte of interest could be a cancer cell and respective analytes could be unique markers on the surface of the cancer cell. One or more properties of the analyte of interest could be determined based on information about the respective analytes determined from information about respective engineered particles.

FIGS. 6B and 8B illustrate paths of the transmitted illumination (662, 862) transmitted by the light source (660, 860) and the emitted energies (652, 852) detected by the energy sensor (650, 850) that do not overlap. However, in some instances, the light source (660, 860) and the energy sensor (650, 850) may be angled towards each other so that they are illuminating and sensing from essentially the same area of subsurface vasculature. Other configurations of light sources, light sensors, light paths, field generators, directed energy fields, and other elements are anticipated. Further, it is anticipated that more than one light source, field generator, or light sensor may be included to enable the embodiments and methods disclosed herein.

IV. Example Wearable Devices

Figure 9:
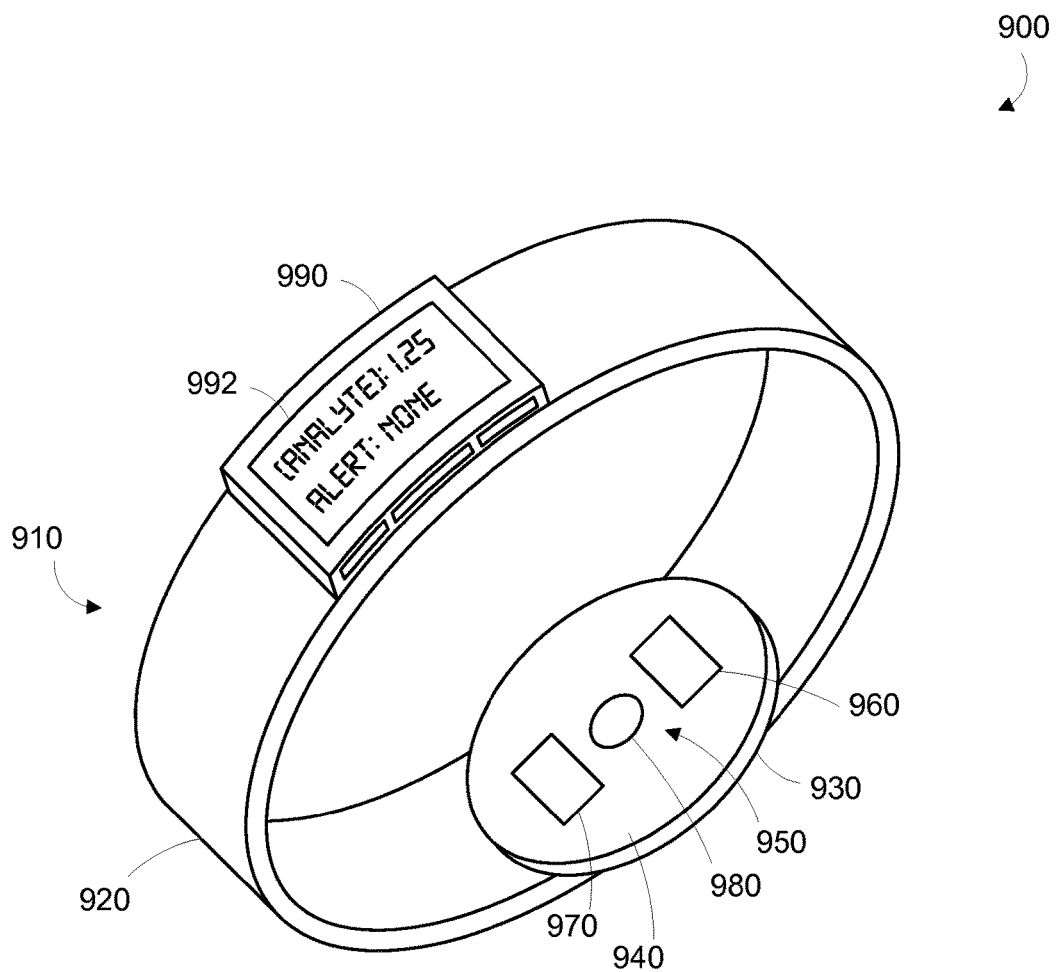
FIG. 9 is a perspective view of an example wearable device.

A wearable device 900 (illustrated in FIG. 9) can automatically measure a plurality of physiological parameters of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 910, such as a belt, wristband, ankle band, etc. can be provided to mount the device at, on or in proximity to the body surface. The mount 910 may prevent the wearable device from moving relative to the body to reduce measurement error and noise. In one example, shown in FIG. 9, the mount 910, may take the form of a strap or band 920 that can be worn around a part of the body. Further, the mount 910 may be an adhesive substrate for adhering the wearable device 900 to the body of a wearer.

A measurement platform 930 is disposed on the mount 910 such that it can be positioned on the body where subsurface vasculature is easily observable. An inner face 940 of the measurement platform is intended to be mounted facing to the body surface. The measurement platform 930 may house a data collection system 950, which may include at least one detector 960 for detecting at least one physiological parameter, which could include any parameters that may relate to the health of the person wearing the wearable device. For example, the detector 960 could be configured to measure blood pressure, pulse rate, respiration rate, skin temperature, etc. In a non-exhaustive list, detector 960 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. The components of the data collection system 950 may be miniaturized so that the wearable device may be worn on the body without significantly interfering with the wearer's usual activities.

At least one of the detectors 960 is an energy sensor configured to detect one or more properties of energy emitted by energy emitters in engineered particles in blood circulating in subsurface vasculature proximate to the wearable device 900. The energy sensor could be a light sensor, an RF sensor, and acoustical sensor, an ultrasonic transducer, or any other sensor or sensors according to the type of energy emitted by the energy emitter of the engineered particles.

In some examples, the energy emitter of the engineered particles emits light energy in response to illumination of the engineered particles, and the energy sensor could be a light sensor. The light sensor could include a filter that is configured to substantially block light emitted by a light source 970 of the data collection system 950. The light sensor could be configured to sense the polarization of light and/or to only detect light of a specified polarization. For example, the light sensor could include a linear polarization filter such that the light sensor only detected light having a polarization aligned with the orientation of the linear polarization filter. In some examples, the detectors 960 could include a first light sensor configured to detect light of a first polarization and a second light sensor configured to detect light of a second polarization, where the second polarization is perpendicular to the first polarization. The first and second detectors could be used to determine an orientation of individual engineered particles in examples where the engineered particles emit light having a specified polarization relative to the orientation of individual engineered particles.

In some examples, the energy emitter of the engineered particles emits acoustical energy in response to illumination of the engineered particles, and the energy sensor could be an acoustical, ultrasonic, or other variety of vibration sensor. The energy sensor could include an impedance matching material positioned between a transducer of the energy sensor and the skin of the wearer. The energy sensor could include a plurality of transducers arranged in a grid or other specified pattern to enable to localization of individual energy emitters in the lumen of subsurface vasculature of the wearer.

The data collection system 950 further includes a light source 970 for transmitting illumination that can penetrate the wearer's skin into the portion of subsurface vasculature, for example, into a lumen of the subsurface vasculature. The transmitted illumination can be any kind of illumination that is benign to the wearer and that results at least in absorption of light energy by optical absorbers in engineered particles proximate to the light source 970. The wavelength of the transmitted illumination could be specified to penetrate biological tissues of a wearer; for example, the transmitted illumination could have a wavelength within a near-infrared (NIR) transparency window of biological tissue. The light source 970 could be configured to produce additional illumination that results in emission of light by other chemicals, imaging agents, biological elements, or other analytes proximate to the light source 970.

The light source 970 could be configured to emit light having a specific polarization relative to the wearable device 900, a wearer of the wearable device, and/or an energy sensor included in the detectors 960. For example, the light source 970 could be configured to emit light of a first linear polarization at a first point in time and to emit light of a second linear polarization, where the second linear polarization is perpendicular to the first polarization, at a second point in time. One or more properties of energy emitted by energy emitters in engineered particles in response to illumination by the light source 970 at the first and second points in time could be detected using the detectors 960. One or more properties of the engineered particles and/or analytes bound to the engineered particles could be determined based on the detected one or more properties of the emitted energy. Other configurations and uses of the light source 970 are anticipated.

In some examples, the light source 970 can be configured to emit light having a wavelength that is twice the wavelength of light necessary to cause the engineered particles to emit energy; that is, the light source 970 can be configured to excite the engineered particles through two-photon absorption. In some examples, the light source 970 can include at least two light-emitting elements. The at least two light-emitting elements could be configured to emit directed light, e.g., the light-emitting elements could be lasers. In some examples, the at least two light-emitting elements produce directed light and the direction of the directed light can be controlled. For example, the at least two light-emitting elements could be lasers whose outputs are reflected off of a MEMS-actuated mirror, such that the emitted laser light is reflected out of the wearable device 900 into tissue of a wearer. The direction of the at least two reflected laser beams could be controlled to scan tissue in proximity to the wearable device 900 by using the MEMS mirrors to control the volume of tissue being illuminated by both reflected laser beams. Other methods of exciting engineered particles using two-photon absorption and/or interrogating a specified volume of an environment containing engineered particles are anticipated.

A directed energy field generator 980 may also be included in the data collection system 950. In such embodiments, the engineered particles may be configured to orient according to a directed energy field that could be generated by the directed energy field generator 980. In some examples, the ability of the engineered particles to orient with a directed energy field, the optical anisotropy of the optical absorbers of the engineered particles, or other properties of the engineered particles could be induced and/or modulated by a directed energy field generated by the directed energy field generator 980. For example, the engineered particles could include optical absorbers comprised of magnetostrictive or electrostrictive materials, and the anisotropy of the optical absorbers could be related to a change in the geometry of the magnetostrictive or electrostrictive materials caused by a magnetic or electric field, respectively, generated by the directed energy field generator 980. Other uses or configurations of the energy field generator are anticipated.

The directed energy field generator 980 could be operated to enable detection of one or more properties of the engineered particles and/or analytes in low signal-to-noise environments, for example, environments that include turbid media, background autofluorescence, and/or high levels of random optical, magnetic, electrical, acoustical, and/or other noise. In some examples, the directed energy field generator 980 could create a directed energy field that changes over time. For example, the directed energy field generator 980 could create a directed energy field that orients the engineered particles, induces optical anisotropy of the engineered particles, or causes some other change in the engineered particles over time, and a related change in the energy emitted by the engineered particles over time could be used to determine one or more properties of the engineered particles and/or the analytes in the environment. In some examples, the directed energy field generator 980 could be operated to generate a directed energy field in an environment of interest such that a specified volume within the environment could be selectively interrogated. For example, the directed energy field generator 980 could generate an RF field in the environment such that only engineered particles in a specific volume of the environment were sufficiently heated to induce a polarization anisotropy of optical absorbers in the engineered particles, enabling the use of polarized light to detect one or more properties of the affected engineered particles and/or target analytes in the specific volume.

In some examples, the directed energy field generator 980 generates a magnetic field, and the engineered particles may also be made of or be functionalized with magnetic materials, such as ferromagnetic, paramagnetic, super-paramagnetic, or any other material that responds to a magnetic field. The energy field generator 980 could be operated to direct a magnetic field into the portion of subsurface vasculature that is sufficient to cause engineered particles to orient themselves relative to the directed magnetic field. The directed magnetic field could additionally or alternatively be used to collect engineered particles proximate to the directed energy field generator 980 to improve the detection of one or more properties of an analyte or according to some other consideration. In some examples, the engineered particles may be configured to have an optical anisotropy, coupling between an optical absorber and an energy emitter, or some other property that is induced, modulated, or otherwise affected by a magnetic field. For example, the engineered particles could include optical absorbers that comprise a magnetostrictive material such that exposure to a directed magnetic field generated by the directed energy field generator 980 causes a change in the geometry of the magnetostrictive materials that, in turn causes a change in the optical anisotropy of the optical absorbers.

In some examples, the directed energy field generator 980 generates an electric field, and the engineered particles may also be made of or be functionalized with materials that exhibit a change or experience a force in response to an electric field, such as electric dipoles, dielectrics, piezoelectrics, or any other material that responds to an electric field. The directed energy field generator 980 could be operated to direct an electric field into the portion of subsurface vasculature that is sufficient to cause engineered particles to orient themselves relative to the directed electric field. In some examples, the engineered particles may be configured to have an optical anisotropy, coupling between an optical absorber and an energy emitter, or some other property that is induced, modulated, or otherwise affected by an electric field. For example, the engineered particles could include optical absorbers that comprise an electrostrictive material such that exposure to a directed electric field generated by the directed energy field generator 980 causes a change in the geometry of the electrostrictive materials that, in turn causes a change in the optical anisotropy of the optical absorbers.

In some examples, the directed energy field generator 980 generates an optical, microwave, RF, infrared, or other electromagnetic field to effect changes in the engineered particles, including but not limited to orienting the engineered particles, inducing a dipole in the engineered particles, and altering an optical anisotropy, energy coupling between an optical absorber and an energy emitter, or some other property of the engineered particles. The directed energy field generator 980 could be operated as 'optical tweezers' to translate or rotate the engineered particles. In some examples, the directed energy field generator 980 could direct an electromagnetic field, e.g. an RF field, toward the engineered particles such that the particles are heated, and the heating of the particles by the electromagnetic field could induce a change in the engineered particles. For example, RF heating of the engineered particles could cause a change in geometry of a bimorph particle.

In some examples, the directed energy field generator 980 generates an acoustic, ultrasonic, or other vibrational energy field to effect changes in the engineered particles, including but not limited to orienting the engineered particles, inducing a dipole in the engineered particles, and altering an optical anisotropy, energy coupling between an optical absorber and an energy emitter, or some other property of the engineered particles. The engineered particles could be configured to have specific vibrational modes (or to include elements having such) relative to the geometry of the engineered particles (e.g., relative to an axis of an optical absorber) such that the engineered particles could orient themselves relative to a local vibrational energy field (e.g., orient themselves perpendicular to a standing wave in an ultrasonic energy field in an environment) that is being created by the directed energy field generator 980.

The directed energy field generator 980 could employ more than one of the methods disclosed herein to control, induce, modulate, or otherwise affect one or more properties of engineered particles in an environment of interest. In an example, an optical field could be used to induce a dipole in the engineered particles, and an electric field could be used to orient the dipole, and by extension, the engineered particles. In another example, RF energy could be used to heat the engineered particles such that the particles could be oriented by a magnetic field. Other examples are anticipated.

The wearable device 900 may also include a user interface 990 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Additionally or alternatively, generated recommendations or alerts could be transmitted, using a communications system of the wearable device 900, to a remote server or other remote system. For example, the generated recommendations or alerts could be transmitted to a user's physician and/or emergency medical personnel. Further, the user interface 990 may include a display 992 where a visual indication of the alert or recommendation may be displayed. The display 992 may further be configured to provide an indication of the measured physiological parameters, for instance, the concentrations of certain blood analytes being measured.

Figure 10A:
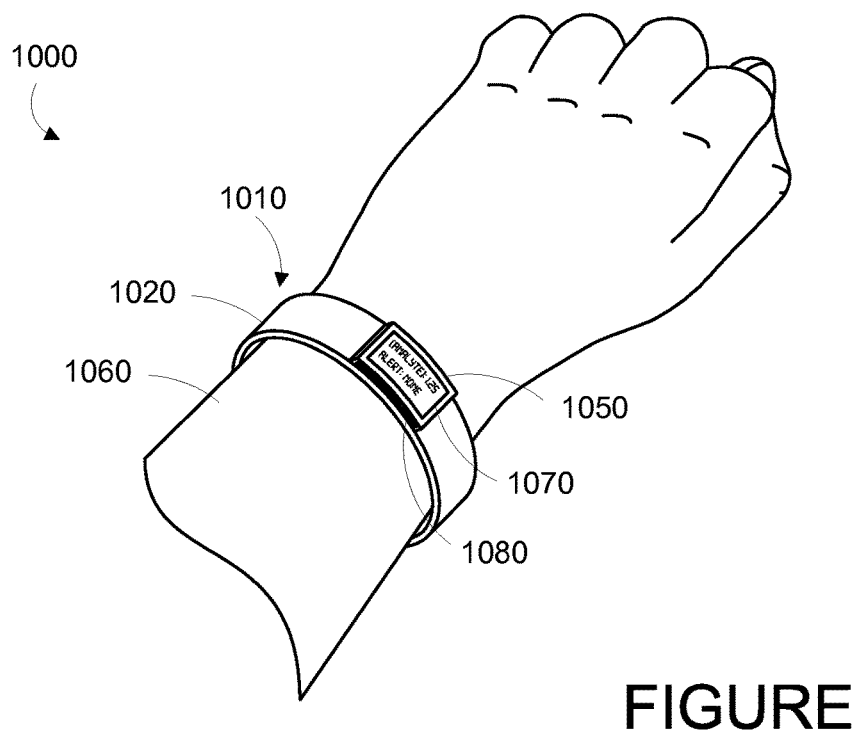
FIG. 10A is a perspective top view of an example wrist-mounted device, when mounted on a wearer's wrist.
Figure 10B:
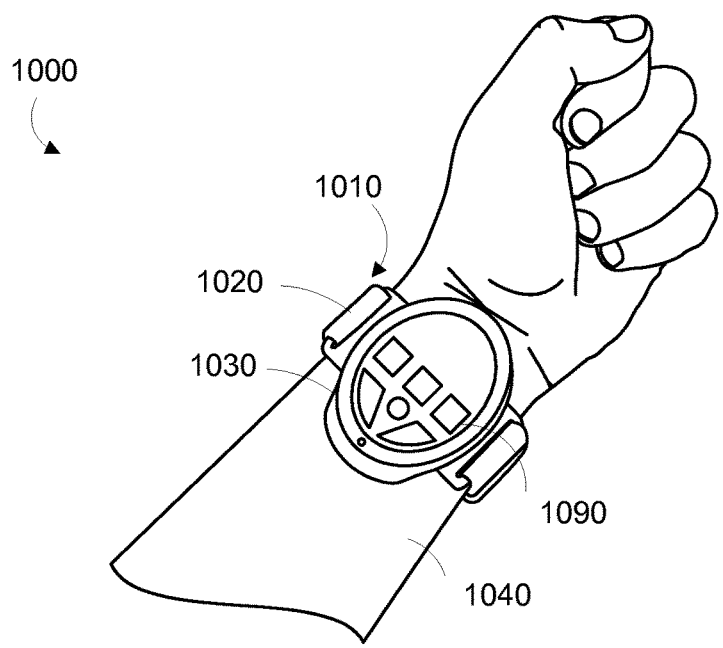
FIG. 10B is a perspective bottom view of an example wrist-mounted device shown in FIG. 10A, when mounted on a wearer's wrist.

In some examples, the wearable device is provided as a wrist-mounted device, as shown in FIGS. 10A, 10B, 11A-11C, 12A, 12B, 13, and 14. The wrist-mounted device may be mounted to the wrist of a living subject with a wristband or cuff, similar to a watch or bracelet. As shown in FIGS. 10A and 10B, the wrist mounted device 1000 may include a mount 1010 in the form of a wristband 1020, a measurement platform 1030 positioned on the anterior side 1040 of the wearer's wrist, and a user interface 1050 positioned on the posterior side 1060 of the wearer's wrist. The wearer of the device may receive, via the user interface 1050, one or more recommendations or alerts generated either from a remote server or other remote computing device, or alerts from the measurement platform. Such a configuration may be perceived as natural for the wearer of the device in that it is common for the posterior side 1060 of the wrist to be observed, such as the act of checking a wrist-watch. Accordingly, the wearer may easily view a display 1070 on the user interface. Further, the measurement platform 1030 may be located on the anterior side 1040 of the wearer's wrist where the subsurface vasculature may be readily observable. However, other configurations are contemplated.

The display 1070 may be configured to display a visual indication of the alert or recommendation and/or an indication of the measured physiological parameters, for instance, the presence or concentrations of certain blood analytes being measured. Further, the user interface 1050 may include one or more buttons 1080 for accepting inputs from the wearer. For example, the buttons 1080 may be configured to change the text or other information visible on the display 1070. As shown in FIG. 10B, measurement platform 1030 may also include one or more buttons 1090 for accepting inputs from the wearer. The buttons 1090 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 11A:
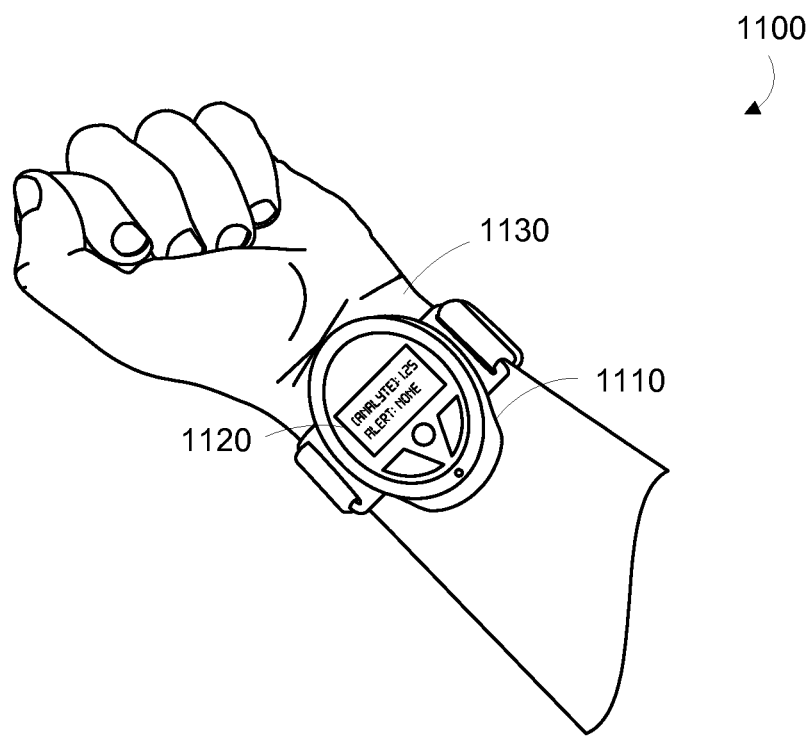
FIG. 11A is a perspective bottom view of an example wrist-mounted device, when mounted on a wearer's wrist.
Figure 11B:
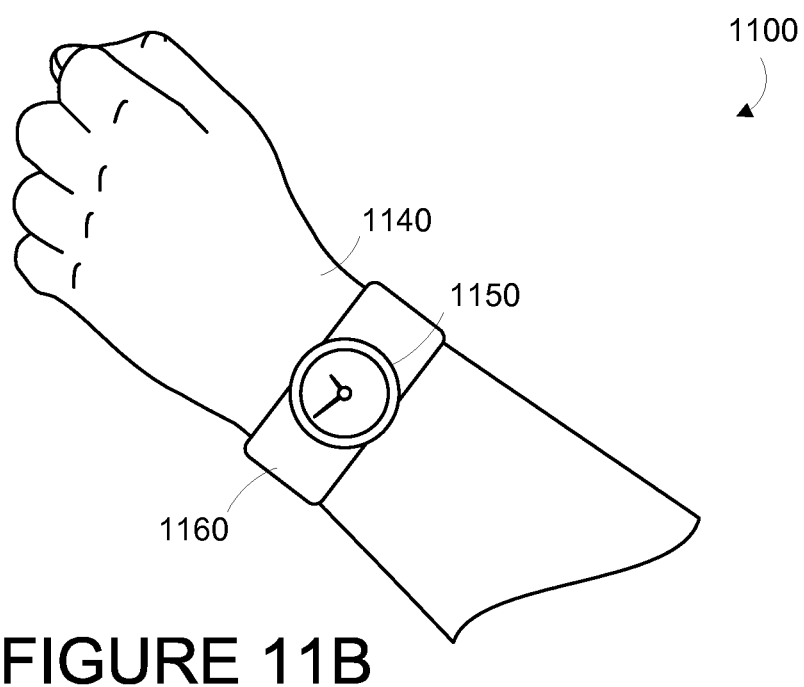
FIG. 11B is a perspective top view of an example wrist-mounted device shown in FIG. 11A, when mounted on a wearer's wrist.
Figure 11C:
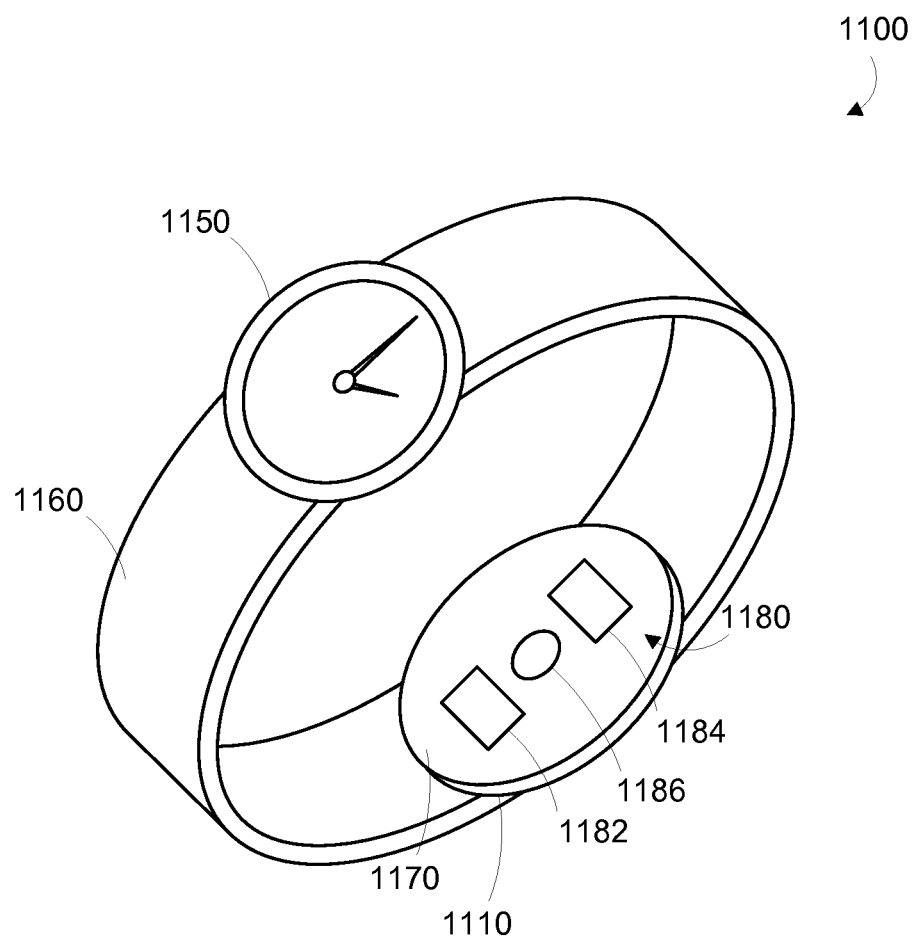
FIG. 11C is a perspective view of an example wrist-mounted device shown in FIGS. 11A and 11B.

In another example wrist-mounted device 1100, shown in FIGS. 11A-11C, the measurement platform 1110 and user interface 1120 are both provided on the same side of the wearer's wrist, in particular, the anterior side 1130 of the wrist. On the posterior side 1140, a watch face 1150 may be disposed on the strap 1160. While an analog watch is depicted in FIG. 11B, one of ordinary skill in the art will recognize that any type of clock may be provided, such as a digital clock.

As can be seen in FIG. 11C, the inner face 1170 of the measurement platform 1110 is intended to be worn proximate to the wearer's body. A data collection system 1180 housed on the measurement platform 1110 may include a detector 1182, a light source 1184, and a directed energy field generator 1186.

Figure 12A:
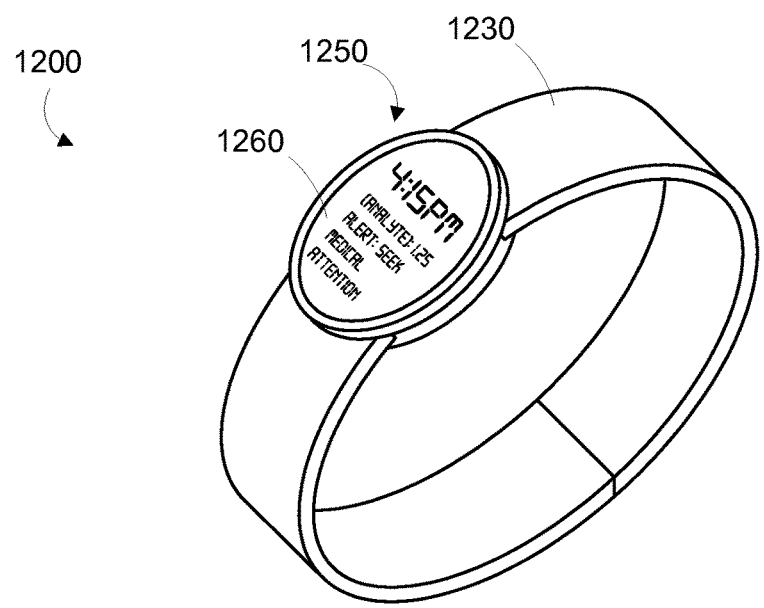
FIG. 12A is a perspective view of an example wrist-mounted device.
Figure 12B:
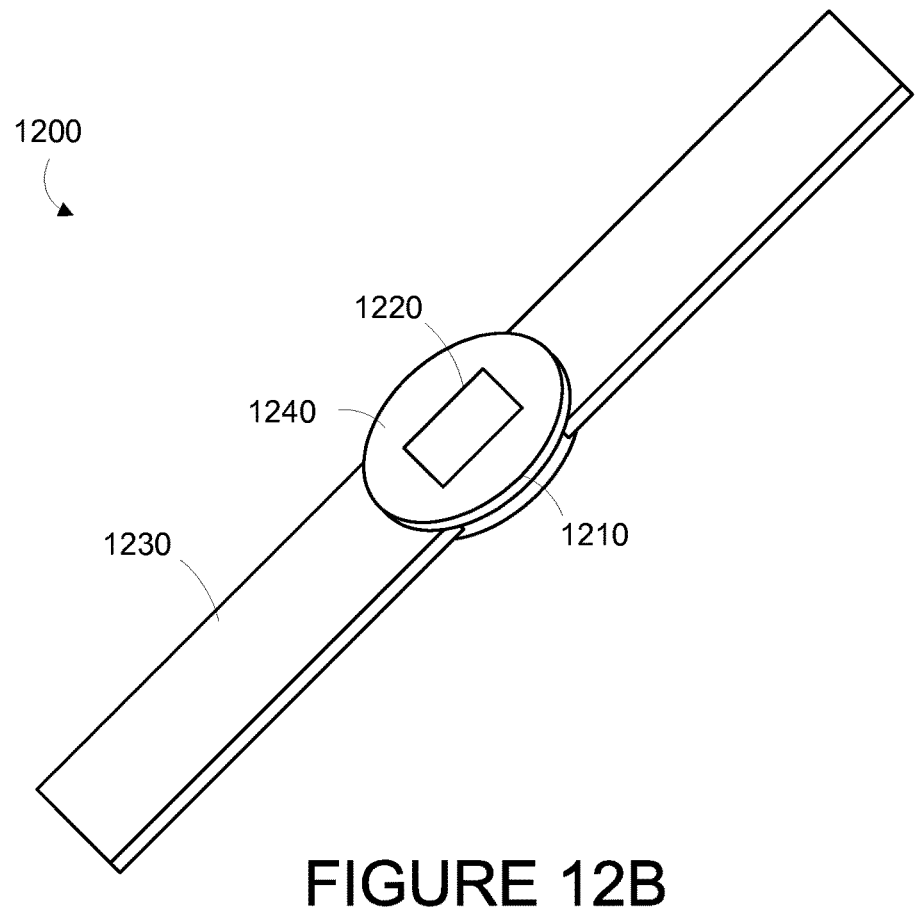
FIG. 12B is a perspective bottom view of an example wrist-mounted device shown in FIG. 12A.

In a further example shown in FIGS. 12A and 12B, a wrist mounted device 1200 includes a measurement platform 1210, which includes a data collection system 1220, disposed on a strap 1230. Inner face 1240 of measurement platform may be positioned proximate to a body surface so that data collection system 1220 may interrogate the subsurface vasculature of the wearer's wrist. A user interface 1250 with a display 1260 may be positioned facing outward from the measurement platform 1210. As described above in connection with other embodiments, user interface 1250 may be configured to display data collected from the data collection system 1220, including the presence and/or concentration of one or more measured analytes, and one or more alerts generated by a remote server or other remote computing device, or a processor located on the measurement platform. The user interface 1220 may also be configured to display the time of day, date, or other information that may be relevant to the wearer.

Figure 13:
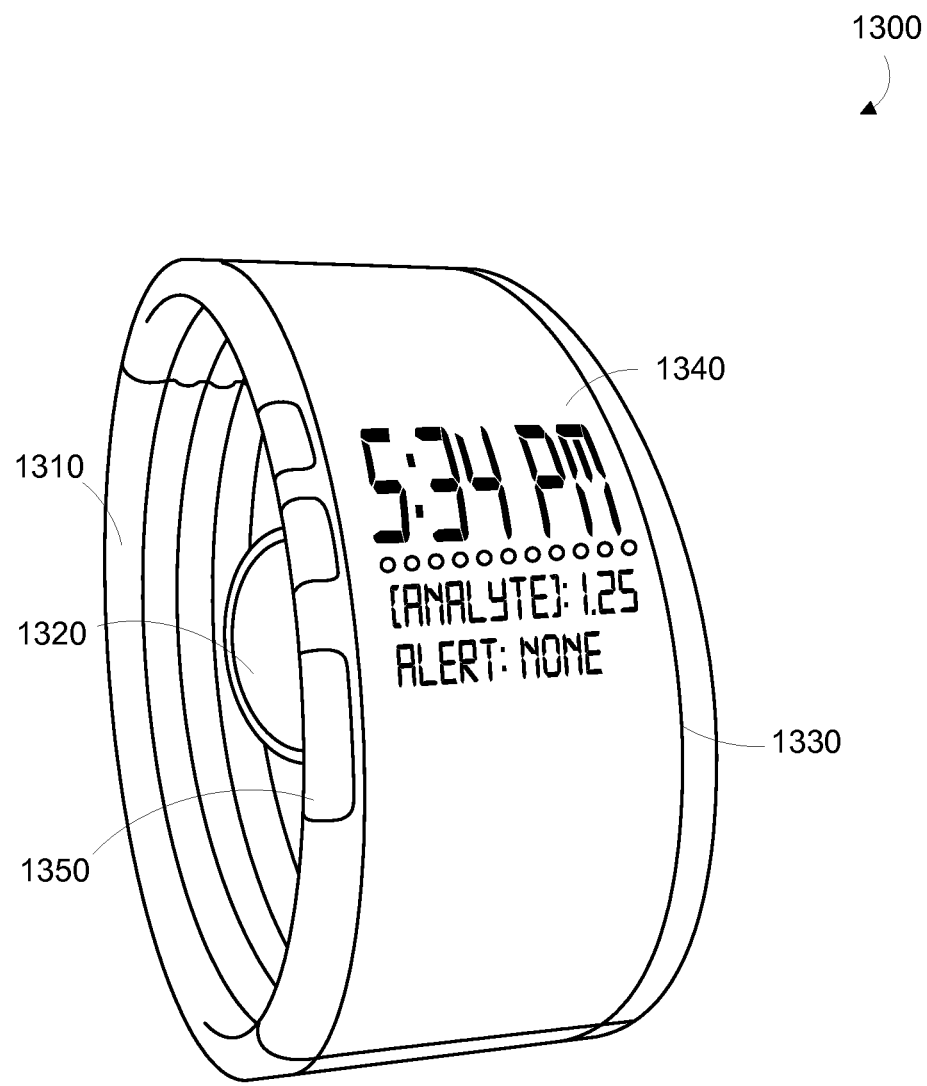
FIG. 13 is a perspective view of an example wrist-mounted device.
Figure 14:
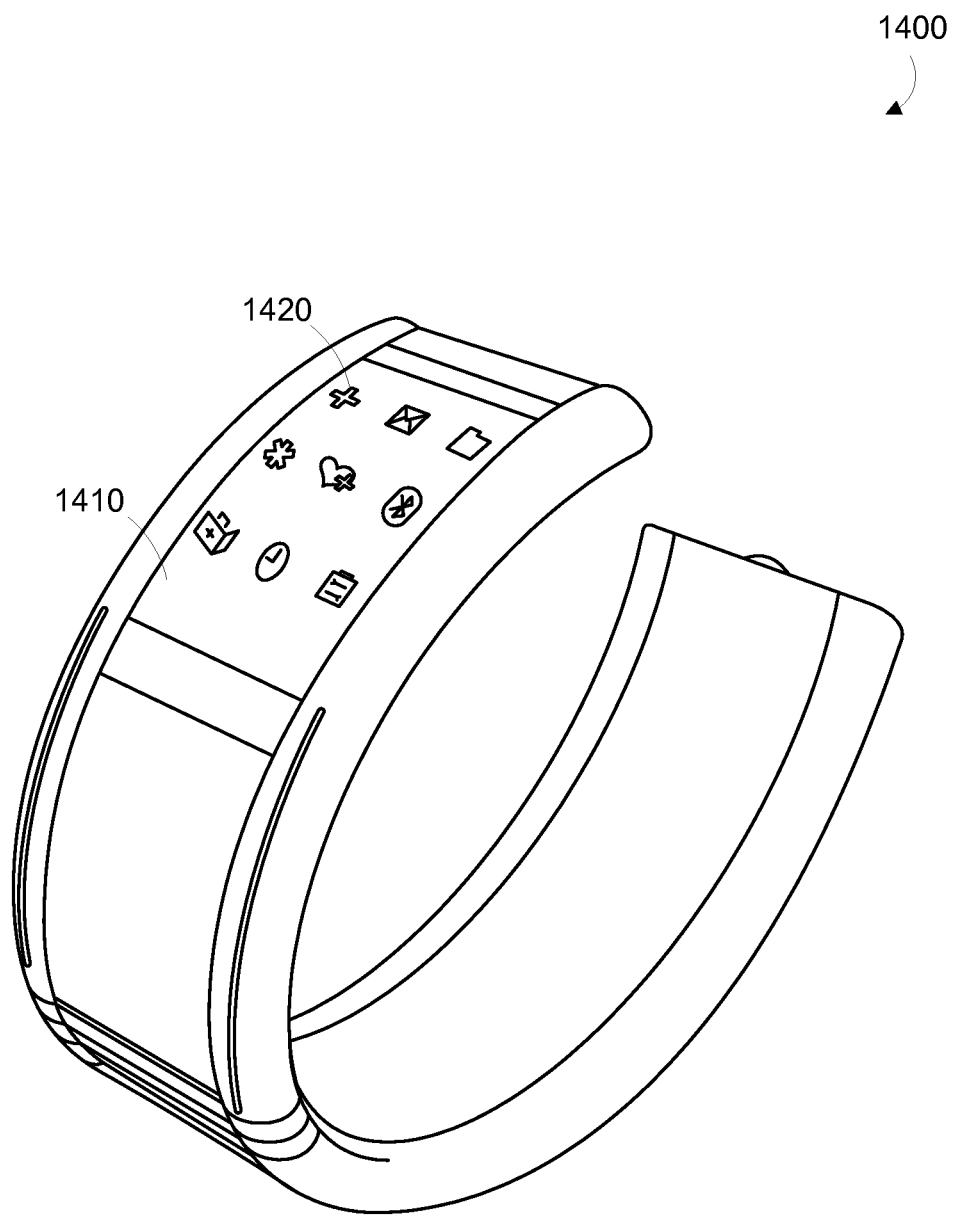
FIG. 14 is a perspective view of an example wrist-mounted device.

As shown in FIG. 13, in a further embodiment, wrist-mounted device 1300 may be provided on a cuff 1310. Similar to the previously discussed embodiments, device 1300 includes a measurement platform 1320 and a user interface 1330, which may include a display 1340 and one or more buttons 1350. The display 1340 may further be a touch-screen display configured to accept one or more input by the wearer. For example, as shown in FIG. 14, display 1410 may be a touch-screen configured to display one or more virtual buttons 1420 for accepting one or more inputs for controlling certain functions or aspects of the device 1400, or inputs of information by the user, such as current health state.

Figure 15:
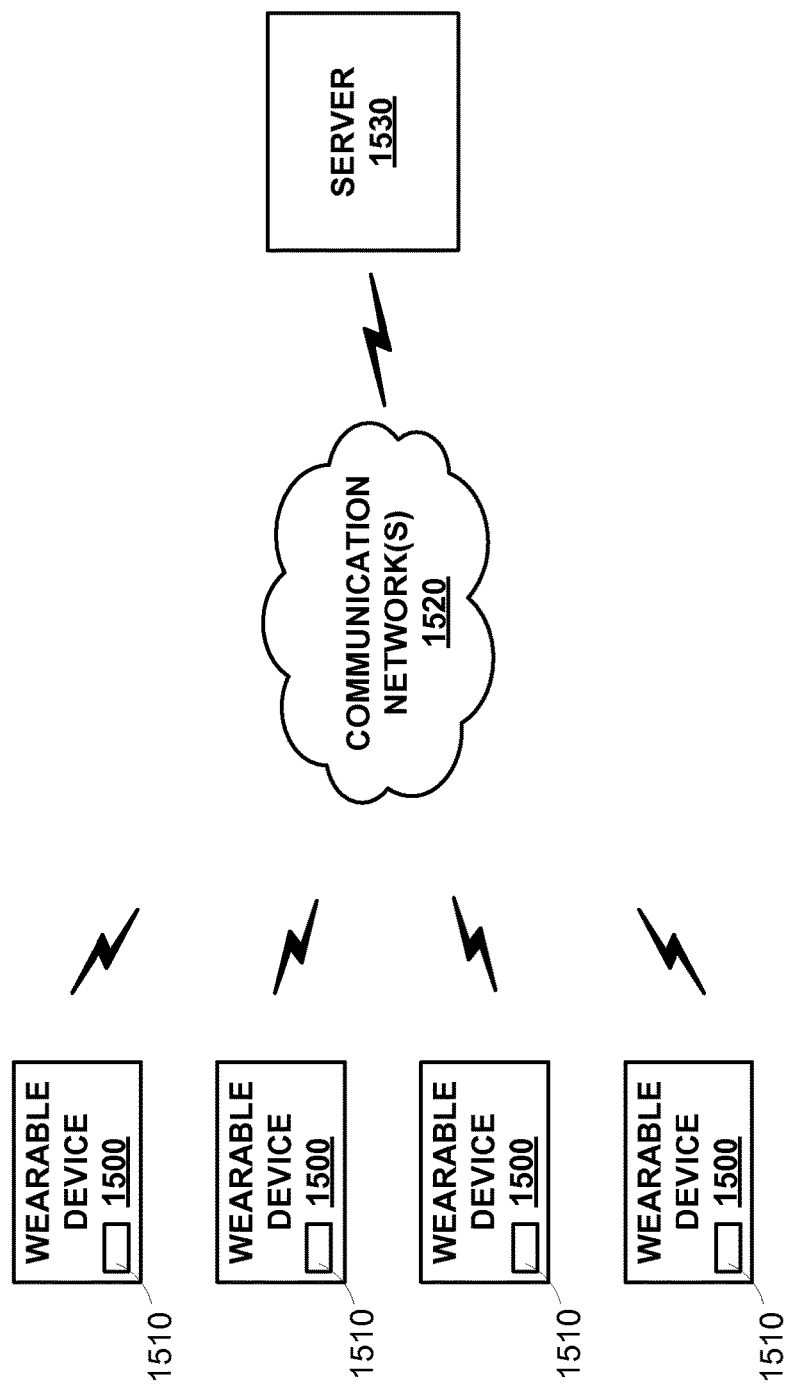
FIG. 15 is a block diagram of an example system that includes a plurality of wearable devices in communication with a server.

FIG. 15 is a simplified schematic of a system including one or more wearable devices 1500. The one or more wearable devices 1500 may be configured to transmit data via a communication interface 1510 over one or more communication networks 1520 to a remote server 1530. In one embodiment, the communication interface 1510 includes a wireless transceiver for sending and receiving communications to and from the server 1530. In further embodiments, the communication interface 1510 may include any means for the transfer of data, including both wired and wireless communications. For example, the communication interface may include a universal serial bus (USB) interface or a secure digital (SD) card interface. Communication networks 1520 may be any one of may be one of: a plain old telephone service (POTS) network, a cellular network, a fiber network and a data network. The server 1530 may include any type of remote computing device or remote cloud computing network. Further, communication network 1520 may include one or more intermediaries, including, for example wherein the wearable device 1500 transmits data to a mobile phone or other personal computing device, which in turn transmits the data to the server 1530.

In addition to receiving communications from the wearable device 1500, such as collected physiological parameter data and data regarding health state as input by the user, the server may also be configured to gather and/or receive either from the wearable device 1500 or from some other source, information regarding a wearer's overall medical history, environmental factors and geographical data. For example, a user account may be established on the server for every wearer that contains the wearer's medical history. Moreover, in some examples, the server 1530 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

V. Example Electronics Platform for a Device

Figure 16:
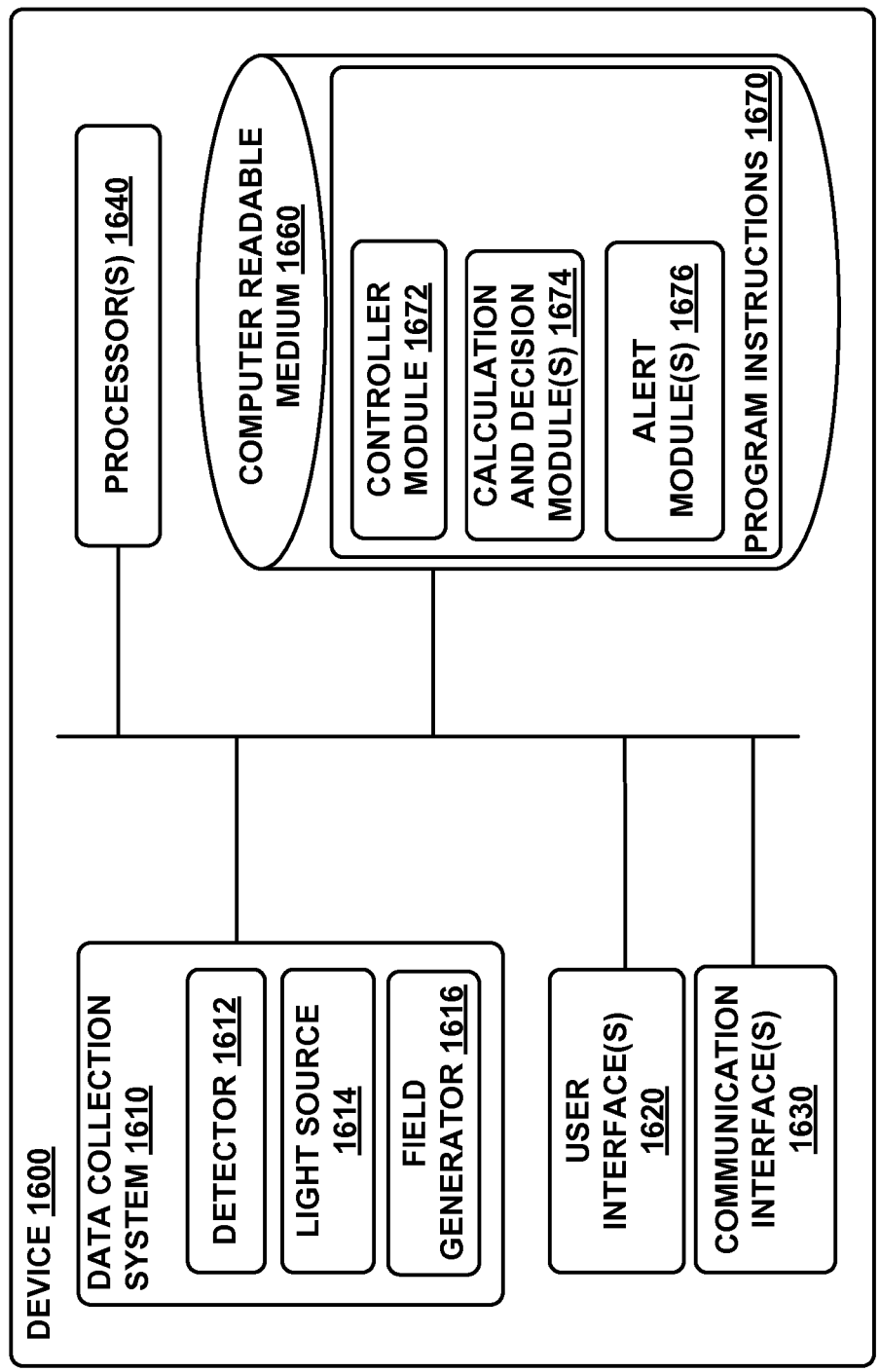
FIG. 16 is a functional block diagram of an example device.

FIG. 16 is a simplified block diagram illustrating the components of a device 1600, according to an example embodiment. Device 1600 may take the form of or be similar to one of the wrist-mounted devices 900, 1000, 1100, 1200, 1300, 1400, shown in FIGS. 9, 10A-B, 11A-11C, 12A-12B, 13 and 14. However, device 1600 may also take other forms, such as an ankle, waist, or chest-mounted device. Device 1600 could also take the form of a device that is not configured to be mounted to a body. For example, device 1600 could take the form of a handheld device configured to be maintained in proximity to an environment of interest (e.g., a body part, a biological sample container, a volume of a water treatment system) by a user or operator of the device 1600 or by a frame or other supporting structure. Device 1600 could also take the form of a device configured to illuminate and to detect emitted light from an in vitro biological environment or some other environment, for example, a fluid volume within a water treatment process. Device 1600 also could take other forms.

In particular, FIG. 16 shows an example of a wearable device 1600 having a data collection system 1610, a user interface 1620, communication interface 1630 for transmitting data to a remote system, and processor(s) 1640. The components of the wearable device 1600 may be disposed on a mount or on some other structure for mounting the device to enable stable detection of one or more properties of engineered particles in an environment of interest, for example, to an external body surface where a portion of subsurface vasculature is readily observable.

Processor 1640 may be a general-purpose processor or a special purpose processor (e.g., digital signal processors, application specific integrated circuits, etc.). The one or more processors 1640 can be configured to execute computer-readable program instructions 1670 that are stored in the computer readable medium 1660 and that are executable to provide the functionality of a device 1600 described herein.

The computer readable medium 1660 may include or take the form of one or more non-transitory, computer-readable storage media that can be read or accessed by at least one processor 1640. The one or more computer-readable storage media can include volatile and/or non-volatile storage components, such as optical, magnetic, organic or other memory or disc storage, which can be integrated in whole or in part with at least one of the one or more processors 1640. In some embodiments, the computer readable medium 1660 can be implemented using a single physical device (e.g., one optical, magnetic, organic or other memory or disc storage unit), while in other embodiments, the computer readable medium 1660 can be implemented using two or more physical devices.

Data collection system 1610 includes detectors 1612, a light source 1614, and a field generator 1616. As described above, detectors 1612 may include any detector capable of detecting at least one biological parameter, which could include any parameters that may relate to the health of a person wearing or otherwise being analyzed by the device. For example, the detectors 1612 could be configured to measure blood pressure, pulse rate, skin temperature, etc. In some examples, detectors 1612 may include one or more of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

At least one of the detectors 1612 is an energy sensor configured to detect one or more properties of energy emitted by energy emitters in engineered particles proximate to the device 1600. The energy sensor could be a light sensor, an RF sensor, and acoustical sensor, an ultrasonic transducer, or any other sensor or sensors according to the type of energy emitted by the energy emitter of the engineered particles.

In some examples, the energy emitter of the engineered particles emits light energy in response to illumination of the engineered particles, and the energy sensor could be a light sensor. The light sensor could include a filter that is configured to substantially block light emitted by the light source 1614 of the data collection system 1610. The light sensor could be configured to sense the polarization of light and/or to only detect light of a specified polarization. For example, the light sensor could include a linear polarization filter such that the light sensor only detected light having a polarization aligned with the orientation of the linear polarization filter. In some examples, the detectors 1612 could include a first light sensor configured to detect light of a first polarization and a second light sensor configured to detect light of a second polarization, where the second polarization is perpendicular to the first polarization. The first and second detectors could be used to determine an orientation of individual engineered particles in examples where the engineered particles emit light having a specified polarization relative to the orientation of individual engineered particles.

In some examples, the energy emitter of the engineered particles emits acoustical energy in response to illumination of the engineered particles, and the energy sensor could be an acoustical, ultrasonic, or other variety of vibration sensor. The energy sensor could include an impedance matching material positioned between a transducer of the energy sensor and environment containing the engineered particles. The energy sensor could include a plurality of transducers arranged in a grid or other specified pattern to enable to localization of individual energy emitters in the environment.

The data collection system 1610 further includes a light source 1614 for transmitting illumination that can penetrate an environment containing functionalized, engineered particles, for example, a lumen of the subsurface vasculature of a user of the device 1600. The transmitted illumination can be any kind of illumination that results at least in emission of energy by energy emitters in engineered particles in the environment. A wavelength of the transmitted illumination could be specified to penetrate biological tissues of a user; for example, the transmitted illumination could have a wavelength within a near-infrared (NIR) transparency window of biological tissue. The light source 1614 could be configured to produce additional illumination that results in emission of light by other chemicals, imaging agents, biological elements, or other analytes proximate to the light source 1614.

The light source 1614 could be configured to emit light having a specific polarization relative to the device 1600, elements of the environment of the device 1600, an environment or organ of a user of the device 1616, and/or a light sensor included in the detectors 1612. For example, the light source 1614 could be configured to emit light of a first linear polarization at a first point in time and to emit light of a second linear polarization, perpendicular to the first polarization, at a second point in time. One or more properties of energy emitted by energy emitters in engineered particles in response to illumination by the light source 1614 at the first and second points in time could be detected using the detectors 1612. One or more properties of the engineered particles and/or analytes bound to the engineered particles could be determined based on the detected one or more properties of the emitted energy. Other configurations and uses of the light source 1614 are anticipated.

In some examples, the light source 1614 can be configured to emit light having a wavelength that is twice the wavelength of light necessary to cause the engineered particles to emit energy; that is, the light source 1614 can be configured to excite the engineered particles through two-photon absorption. In some examples, the light source 1614 can include at least two light-emitting elements. The at least two light-emitting elements could be configured to emit directed light, e.g., the light-emitting elements could be lasers. In some examples, the at least two light-emitting elements produce directed light and the direction of the directed light can be controlled. For example, the at least two light-emitting elements could be lasers whose outputs we reflected off of a MEMS-actuated mirror, such that the emitted laser light is reflected out of the device 1600 into an environment being interrogated. The direction of the at least two reflected laser beams could be controlled to scan the environment in proximity to the device 1600 by using the MEMS mirrors to control the volume of the environment being illuminated by at least two reflected laser beams. The direction of beams of light could be controlled by other means, for example, by using mirrors or other optical elements mounted on galvanometers. Other methods of exciting engineered particles using two-photon absorption and/or interrogating a specified volume of an environment containing engineered particles are anticipated.

A field generator 1616 may also be included in the data collection system 1610. In such embodiments, the engineered particles may be configured to orient according to a directed energy field that could be generated by the field generator 1616. In some examples, the ability of the engineered particles to orient with a directed energy field, the optical anisotropy of the optical absorbers of the engineered particles, or other properties of the engineered particles could be induced and/or modulated by a directed energy field generated by the field generator 1616. For example, the engineered particles could include optical absorbers comprised of magnetostrictive or electrostrictive materials, and the anisotropy of the optical absorbers could be related to a change in the geometry of the magnetostrictive or electrostrictive materials caused by a magnetic or electric field, respectively, generated by the field generator 1616. Other uses or configurations of the energy field generator are anticipated.

The field generator 1616 could be operated to enable detection of one or more properties of the engineered particles and/or analytes in low signal-to-noise environments, for example, environments that include turbid media, background autofluorescence, and/or high levels of random optical, magnetic, electrical, acoustical, and/or other noise. In some examples, the field generator 1616 could create a directed energy field that changed over time. For example, the field generator 1616 could create a directed energy field that oriented the engineered particles, induced optical anisotropy of the engineered particles, or caused some other change in the engineered particles over time, and a related change in the energy emitted by the engineered particles over time could be used to determine one or more properties of the engineered particles and/or the analytes in the environment. In some examples, the energy field generator 1616 could be operated to generate a directed energy field in an environment of interest such that a specified volume within the environment could be selectively interrogated. For example, the energy field generator 1616 could generate an RF field in the environment such that only engineered particles in a specific volume of the environment were sufficiently heated to induce a polarization anisotropy of optical absorbers in the engineered particles, enabling the use of polarized light to detect one or more properties of the affected engineered particles and/or target analytes in the specific volume.

In some examples, the field generator 1616 generates a magnetic field, and the engineered particles may also be made of or be functionalized with magnetic materials, such as ferromagnetic, paramagnetic, super-paramagnetic, or any other material that responds to a magnetic field. The field generator 1616 could be operated to direct a magnetic field into the portion of subsurface vasculature that is sufficient to cause engineered particles to orient themselves relative to the directed magnetic field. The directed magnetic field could additionally or alternatively be used to collect engineered particles proximate to the field generator 1616 to improve the detection of one or more properties of an analyte or according to some other consideration. In some examples, the engineered particles may be configured to have an optical anisotropy, coupling between an optical absorber and an energy emitter, or some other property that is induced, modulated, or otherwise affected by a magnetic field. For example, the engineered particles could include optical absorbers that comprise a magnetostrictive material such that exposure to a directed magnetic field generated by the field generator 1616 causes a change in the geometry of the magnetostrictive materials that, in turn causes a change in the optical anisotropy of the optical absorbers.

In some examples, the field generator 1616 generates an electric field, and the engineered particles may also be made of or be functionalized with materials that exhibit a change or experience a force in response to an electric field, such as electric dipoles, dielectrics, piezoelectrics, or any other material that responds to an electric field. The field generator 1616 could be operated to direct an electric field into the portion of subsurface vasculature that is sufficient to cause engineered particles to orient themselves relative to the directed electric field. In some examples, the engineered particles may be configured to have an optical anisotropy, coupling between an optical absorber and an energy emitter, or some other property that is induced, modulated, or otherwise affected by an electric field. For example, the engineered particles could include optical absorbers that comprise an electrostrictive material such that exposure to a directed electric field generated by the field generator 1616 causes a change in the geometry of the electrostrictive materials that, in turn causes a change in the optical anisotropy of the optical absorbers.

In some examples, the field generator 1616 generates an optical, microwave, RF, infrared, or other electromagnetic field to effect changes in the engineered particles, including but not limited to orienting the engineered particles, inducing a dipole in the engineered particles, and altering an optical anisotropy, energy coupling between an optical absorber and an energy emitter, or some other property of the engineered particles. The field generator 1616 could be operated as 'optical tweezers' to translate or rotate the engineered particles. In some examples, the field generator 1616 could direct an electromagnetic field, e.g. an RF field, toward the engineered particles such that the particles are heated, and the heating of the particles by the electromagnetic field could induce a change in the engineered particles. For example, RF heating of the engineered particles could cause a change in geometry of a bimetallic bimorph.

In some examples, the field generator 1616 generates an acoustic, ultrasonic, or other vibrational energy field to effect changes in the engineered particles, including but not limited to orienting the engineered particles, inducing a dipole in the engineered particles, and altering an optical anisotropy, energy coupling between an optical absorber and an energy emitter, or some other property of the engineered particles. The engineered particles could be configured to have specific vibrational modes (or to include elements having such) relative to the geometry of the engineered particles (e.g., relative to an axis of an optical absorber) such that the engineered particles could orient themselves relative to a local vibrational energy field (e.g., orient themselves perpendicular to a standing wave in an ultrasonic energy field in an environment) that is being created by the field generator 1616.

The field generator 1616 could employ more than one of the methods disclosed herein to control, induce, modulate, or otherwise affect one or more properties of engineered particles in an environment of interest. In an example, an optical field could be used to induce a dipole in the engineered particles, and an electric field could be used to orient the dipole, and by extension, the engineered particles. In another example, RF energy could be used to heat the engineered particles such that the particles could be oriented by a magnetic field. Other examples are anticipated.

The program instructions 1670 stored on the computer readable medium 1660 may include instructions to perform or facilitate some or all of the device functionality described herein. For instance, in the illustrated embodiment, program instructions 1670 include a controller module 1672, calculation and decision module 1674 and an alert module 1676.

The controller module 1672 can include instructions for operating the data collection system 1610, for example, the detectors 1612, light source 1614, and field generator 1616. For example, the controller module 1672 may operate light source 1614, field generator 1616, and/or detectors 1612 during each of a set of pre-set measurement periods. In particular, the controller module 1672 can include instructions for operating the light source 1614 to emit illumination into a tissue of a wearer of the wearable device 1600 and controlling the detectors 1612 to detect one or more properties of light emitted by energy emitters in engineered particles in the environment being interrogated by the device 1600.

The controller module 1672 can also include instructions for operating a user interface 1620. For example, controller module 1672 may include instructions for displaying data collected by the data collection system 1610 and analyzed by the calculation and decision module 1674, or for displaying one or more alerts generated by the alert module 1675. Further, controller module 1672 may include instructions to execute certain functions based on inputs accepted by the user interface 1620, such as inputs accepted by one or more buttons disposed on the user interface.

Communication platform 1630 may also be operated by instructions within the controller module 1672, such as instructions for sending and/or receiving information via a wireless antenna, which may be disposed on or in the device 1600. The communication interface 1630 can optionally include one or more oscillators, mixers, frequency injectors, etc. to modulate and/or demodulate information on a carrier frequency to be transmitted and/or received by the antenna. In some examples, the device 1600 is configured to indicate an output from the processor by modulating an impedance of the antenna in a manner that is perceivable by a remote server or other remote computing device.

Calculation and decision module 1672 may include instructions for receiving data from the data collection system 1610, analyzing the data to determine if a target analyte is present or absent, quantify the measured physiological parameter(s), such as concentration of a target analyte, analyzing the data to determine if a medical condition is indicated, or other analytical processes relating to the environment proximate to the device 1600. In particular, the calculation and decision module 1672 may include instructions for determining, for each preset measurement time, the presence, concentration, and/or other properties of a clinically-relevant analyte based on the one or more properties of energy emitted by energy emitters in engineered particles in the lumen of the subsurface vasculature of a user of the device 1600; and determining whether a medical condition is indicated based on at least the corresponding presence, concentration, or other property of the clinically-relevant analyte. These instructions could be executed at each of a set of preset measurement times.

The program instructions of the calculation and decision module 1672 may, in some examples, be stored in a computer-readable medium and executed by a processor located external to the device 1600. For example, the device 1600 could be configured to collect certain data regarding physiological parameters from the user and then transmit the data to a remote server, which may include a mobile device, a personal computer, the cloud, or any other remote system, for further processing.

The computer readable medium 1660 may further contain other data or information, such as medical and health history of a user of the device 1600, that may be useful in determining whether a medical condition is indicated. Further, the computer readable medium 1660 may contain data corresponding to certain analyte baselines, above or below which a medical condition is indicated. The baselines may be pre-stored on the computer readable medium 1660, may be transmitted from a remote source, such as a remote server, or may be generated by the calculation and decision module 1674 itself. The calculation and decision module 1674 may include instructions for generating individual baselines for the user of the device 1600 based on data collected over a certain number of measurement periods. For example, the calculation and decision module 1674 may generate a baseline concentration of a target blood analyte for each of a plurality of measurement periods by averaging the analyte concentration at each of the measurement periods measured over the course of a few days, and store those baseline concentrations in the computer readable medium 1660 for later comparison. Baselines may also be generated by a remote server and transmitted to the device 1600 via communication interface 1630. The calculation and decision module 1674 may also, upon determining that a medical condition is indicated, generate one or more recommendations for the user of the device 1600 based, at least in part, on consultation of a clinical protocol. Such recommendations may alternatively be generated by the remote server and transmitted to the device 1600.

In some examples, the collected physiological parameter data, baseline profiles, health state information input by device users and generated recommendations and clinical protocols may additionally be input to a cloud network and be made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 1674 that a medical condition is indicated, the alert module 1676 may generate an alert via the user interface 1620. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A contrast agent comprising a plurality of engineered particles, wherein each engineered particle of the contrast agent comprises:
   a bioreceptor, wherein the bioreceptor selectively interacts with an analyte;
   at least one conductive nanorod, wherein the at least one conductive nanorod absorbs polarized electromagnetic radiation that is aligned with an axis of the at least one conductive nanorod more than polarized electromagnetic radiation that is not aligned with the axis of the at least one conductive nanorod, wherein the conductive nanorod transduces a portion of electromagnetic energy received by the at least one conductive nanorod into a surface plasmon resonance, wherein the surface plasmon resonance generates a time-varying electric field around the conductive nanorod; and at least one light emitter, wherein the at least one light emitter is located within the time-varying electric field that is generated around the conductive nanorod when the conductive nanorod transduces a portion of received electromagnetic energy into a surface plasmon resonance, and wherein the at least one light emitter transduces a time-varying electromagnetic field to which it is exposed into emitted light energy.

2. The contrast agent of claim 1, wherein the conductive nanorod is attached to a first region of the bioreceptor and the light emitter is attached to a second region of the bioreceptor, and wherein the bioreceptor undergoes a conformational change in response to interacting with the analyte such that a distance between the first region of the bioreceptor and the second region of the bioreceptor is related to whether the bioreceptor is interacting with the analyte.

3. The contrast agent of claim 1, wherein the at least one light emitter comprises a fluorophore.

4. The contrast agent of claim 1, wherein the at least one light emitter comprises a quantum dot.

5. The contrast agent of claim 1, wherein the conductive nanorod comprises superparamagnetic iron oxide coated in gold.

6. The contrast agent of claim 1, wherein each engineered particle of the contrast agent further comprises a particle of superparamagnetic iron oxide, wherein the particle of superparamagnetic iron oxide experiences a torque when exposed to a magnetic field.

7. The contrast agent of claim 1, wherein the bioreceptor and the light emitter are disposed on a surface of the conductive nanorod.

8. The contrast agent of claim 1, wherein the bioreceptor comprises a protein, and wherein the light emitter comprises a fluorescent moiety of the protein.

9. The contrast agent of claim 8, wherein the bioreceptor comprises a single recombinant protein.

10. The contrast agent of claim 1, wherein the light emitter comprises a Raman dye.

11. The contrast agent of claim 1, wherein the bioreceptor comprises an antibody.

12. The contrast agent of claim 1, wherein the bioreceptor comprises an aptamer.

* * * * *